(12) United States Patent
Matsumoto

(10) Patent No.: US 12,213,839 B2
(45) Date of Patent: Feb. 4, 2025

(54) ULTRASOUND DIAGNOSTIC APPARATUS AND METHOD OF CONTROLLING ULTRASOUND DIAGNOSTIC APPARATUS

(71) Applicant: FUJIFILM Corporation, Tokyo (JP)

(72) Inventor: Tsuyoshi Matsumoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 382 days.

(21) Appl. No.: 17/669,051

(22) Filed: Feb. 10, 2022

(65) Prior Publication Data
US 2022/0160335 A1   May 26, 2022

Related U.S. Application Data

(63) Continuation of application No. PCT/JP2020/025859, filed on Jul. 1, 2020.

(30) Foreign Application Priority Data

Aug. 15, 2019   (JP) .................................. 2019-149054

(51) Int. Cl.
*A61B 8/00*   (2006.01)
*A61B 8/08*   (2006.01)
*A61B 8/14*   (2006.01)

(52) U.S. Cl.
CPC .............. *A61B 8/54* (2013.01); *A61B 8/0841* (2013.01); *A61B 8/085* (2013.01); *A61B 8/14* (2013.01);
(Continued)

(58) Field of Classification Search
CPC ......... A61B 8/0841; A61B 8/085; A61B 8/14; A61B 8/4488; A61B 8/461; A61B 8/463; A61B 8/52; A61B 8/5223; A61B 8/54
See application file for complete search history.

(56) References Cited

U.S. PATENT DOCUMENTS 6,119,033 A * 9/2000 Spigelman ............. A61B 90/36
                                                              600/426
6,132,379 A   10/2000 Patacsil et al.
(Continued)

FOREIGN PATENT DOCUMENTS

CN   103930041 A   7/2014
CN   106061424 A   10/2016
(Continued)

OTHER PUBLICATIONS

Translated Copy of Watanabe JP2018023610A (Year: 2018).*
(Continued)

*Primary Examiner* — Katherine L Fernandez
*Assistant Examiner* — Brooke Lyn Klein
(74) *Attorney, Agent, or Firm* — Studebaker & Brackett PC

(57) ABSTRACT

Provided are an ultrasound diagnostic apparatus capable of appropriately highlighting a blood vessel in an ultrasound image depending on an insertion situation of an insert, and a method of controlling the same.
An ultrasound diagnostic apparatus 1 includes a transducer array 2, an image acquisition unit 11 that acquires an ultrasound image, a display device 8 that displays the ultrasound image, an image analysis unit 9 that analyzes the ultrasound image to detect a blood vessel and an insert in the ultrasound image, a highlighting unit 10 that highlights the blood vessel detected by the image analysis unit 9 in displaying the ultrasound image, and an apparatus controller 13 that controls the highlighting unit 10. The apparatus controller 13 performs control such that the highlighting unit 10 changes a form in highlighting the blood vessel depending on a relative positional relationship between the blood vessel and the insert.

18 Claims, 20 Drawing Sheets

(52) U.S. Cl.
CPC ............ *A61B 8/4488* (2013.01); *A61B 8/461* (2013.01); *A61B 8/463* (2013.01)

(56) References Cited

U.S. PATENT DOCUMENTS

| | | | |
|---|---|---|---|
| 2004/0151358 A1* | 8/2004 | Yanagita | G06T 7/0012 |
| | | | 382/132 |
| 2007/0073155 A1 | 3/2007 | Park et al. | |
| 2015/0245819 A1 | 9/2015 | Yoshiara et al. | |
| 2016/0317118 A1 | 11/2016 | Parthasarathy et al. | |
| 2016/0317119 A1 | 11/2016 | Tahmasebi Maraghoosh et al. | |
| 2017/0119352 A1 | 5/2017 | Anand | |
| 2017/0196535 A1* | 7/2017 | Arai | A61B 8/466 |
| 2022/0104789 A1 | 4/2022 | Matsumoto et al. | |

FOREIGN PATENT DOCUMENTS

| | | |
|---|---|---|
| CN | 106413565 A | 2/2017 |
| CN | 114144120 A | 3/2022 |
| JP | 2014-113481 A | 6/2014 |
| JP | 2015-013069 A | 1/2015 |
| JP | 2017-503548 A | 2/2017 |
| JP | 2018023610 A * | 2/2018 |
| WO | WO-2020045065 A1 * | 3/2020 |

OTHER PUBLICATIONS

Translated copy of Hitoshi WO 2020034065 (Year: 2020).*
An Office Action issued by the State Intellectual Property Office of the People's Republic of China on Nov. 6, 2023, which corresponds to Chinese Patent Application No. CN 202080057348.8.
International Search Report issued in PCT/JP2020/025859; mailed Sep. 8, 2020.
International Preliminary Report On Patentability and Written Opinion issued in PCT/JP2020/025859; issued Feb. 8, 2022.
Csurka et al.: Visual Categorization with Bags of Keypoints, Proc. of ECCV Workshop on Statistical Learning in Computer Vision, pp. 1-16, (2004).
Krizhevsky et al.: ImageNet Classification with Deep Convolutional Neural Networks, Advances in Neural Information Processing Systems 25, pp. 1-9, (2012).
The extended European search report issued by the European Patent Office on Aug. 12, 2022, which corresponds to European Application No. 20851683.1-1126 and is related to U.S. Appl. No. 17/669,051.
The extended European search report issued by the European Patent Office on Feb. 7, 2024, which corresponds to European Application No. 23211658.2 and is related to U.S. Appl. No. 17/669,051.

* cited by examiner

ULTRASOUND DIAGNOSTIC APPARATUS AND METHOD OF CONTROLLING ULTRASOUND DIAGNOSTIC APPARATUS

CROSS-REFERENCE TO RELATED APPLICATIONS

This application is a Continuation of PCT International Application No. PCT/JP2020/025859 filed on Jul. 1, 2020, which claims priority under 35 U.S.C. § 119(a) to Japanese Patent Application No. 2019-149054 filed on Aug. 15, 2019. The above application is hereby expressly incorporated by reference, in its entirety, into the present application.

BACKGROUND OF THE INVENTION

1. Field of the Invention

The present invention relates to an ultrasound diagnostic apparatus that displays a blood vessel of a subject and an insert inserted into the blood vessel in an ultrasound image, and a method of controlling an ultrasound diagnostic apparatus.

2. Description of the Related Art

Hitherto, as an apparatus that obtains an image of the inside of a subject, an ultrasound diagnostic apparatus is known. In general, the ultrasound diagnostic apparatus has an ultrasound probe comprising a transducer array in which a plurality of ultrasound transducers are arranged. An ultrasound beam is transmitted from the transducer array toward the inside of the subject in a state in which the ultrasound probe is brought into contact with a body surface of the subject, and in a case where an ultrasound echo generated inside the subject is received in the transducer array, an electric signal corresponding to the ultrasound echo is acquired. The ultrasound diagnostic apparatus processes the acquired electric signal to generate an ultrasound image of a concerned part of the subject.

Incidentally, there is known a procedure for inserting an insert, such as a puncture needle and a catheter, into a blood vessel of a subject while observing the inside of the subject using the above-described ultrasound diagnostic apparatus, specifically, an echo guided puncture method. In the echo guided puncture method, usually, an operator recognizes the position, shape, and the like of the blood vessel inside the subject through an ultrasound image; however, a given level or higher of skill is required to accurately recognize the position, shape, and the like of the blood vessel. In the echo guided puncture method, since the operator holds the ultrasound probe with one hand, moves the ultrasound probe to a position where the blood vessel is rendered in the ultrasound image, and inserts the insert toward the blood vessel with the other hand, a level of difficulty of work is extremely high and concentration is required.

In the echo guided puncture method, to confirm that the insert correctly enters the blood vessel, the operator needs to recognize a relative positional relationship between a vascular wall and the insert in the ultrasound image or to determine whether or not the insert is inserted into the blood vessel from minute movement or the like of the vascular wall. Here, the operator alternately sees an inserted point of the insert in the subject and confirms the ultrasound image. Note that a B mode image as an ultrasound image is usually displayed on a gray scale, and thus, the blood vessel and the insert in the ultrasound image are hardly identified at a glance.

For this reason, for example, as disclosed in JP2017-503548A, an ultrasound diagnostic apparatus that automatically detects an insert (specifically, medical appliance, such as a needle) in an ultrasound image and displays the ultrasound image with the detected insert visually highlighted has been developed. In a case where such an apparatus is used, the visibility of the insert in the ultrasound image is improved. In a case where the technique described in JP2017-503548A is applied, for example, the blood vessel in the ultrasound image can be detected, and the detected blood vessel can be highlighted. With this, the visibility of the blood vessel in the ultrasound image is improved.

SUMMARY OF THE INVENTION

Incidentally, in a case of highlighting the blood vessel in the ultrasound image in the echo guided puncture method, it is desirable to appropriately highlight the blood vessel in light of an insertion state of the insert (specifically, change of a distal end position of the insert, or the like). However, even though the technique described in JP2017-503548A is used, while the detected blood vessel and insert can be highlighted, it is difficult to realize highlighting depending on the insertion state of the insert.

The present invention has been accomplished in view of the above-described situation, and is to solve the following object.

To solve the problems in the related art described above, an object of the present invention is to provide an ultrasound diagnostic apparatus capable of appropriately highlighting a blood vessel in an ultrasound image depending on an insertion state of an insert, and a method of controlling the same.

To achieve the above-described object, the present invention provides an ultrasound diagnostic apparatus that displays a blood vessel of a subject and an insert inserted into the blood vessel in an ultrasound image, the ultrasound diagnostic apparatus comprising a transducer array, an image acquisition unit that causes the transducer array to transmit an ultrasound beam toward the subject and receives an ultrasound echo generated inside the subject to acquire the ultrasound image, a display device that displays the ultrasound image acquired by the image acquisition unit, an image analysis unit that analyzes the ultrasound image acquired by the image acquisition unit to detect the blood vessel and the insert in the ultrasound image, a highlighting unit that highlights the blood vessel detected by the image analysis unit in a case where the ultrasound image is displayed on the display device, and an apparatus controller that performs control such that the highlighting unit changes a form in highlighting the blood vessel depending on a relative positional relationship between the blood vessel and the insert detected by the image analysis unit.

In the ultrasound diagnostic apparatus of the present invention described above, the image analysis unit may specify a physical quantity representing the relative positional relationship between the detected blood vessel and insert, and the apparatus controller may perform control such that, in a case where the physical quantity specified by the image analysis unit is greater than a threshold value, the highlighting unit highlights the blood vessel in a first form, and in a case where the physical quantity specified by the image analysis unit is smaller than the threshold value, the highlighting unit highlights the blood vessel in a second form different from the first form. In this case, it is preferable that the second form is a form in which the blood vessel is highlighted while avoiding interference with the blood vessel detected by the image analysis unit.

In the configuration described above, the image analysis unit may specify, as the physical quantity, a distance between the detected blood vessel and insert or an insertion angle of the insert with respect to the detected blood vessel.

In the ultrasound diagnostic apparatus of the present invention, the first form may correspond to at least one of a form in which the blood vessel is displayed to be filled with a highlight color, a form in which a contour of the blood vessel is displayed in the highlight color, a form in which a character string is displayed at a position overlapping the blood vessel, or a form in which an instruction mark of the blood vessel is displayed around the blood vessel, and the second form may correspond to at least one of a form in which the instruction mark is displayed around the blood vessel while being separated from the blood vessel in the ultrasound image, a form in which the blood vessel is enlarged and displayed, a form in which the blood vessel in the ultrasound image is displayed with brightness brighter than a vicinity, a form in which a filling layer of the highlight color set to transmittance such that a tomographic image of the blood vessel is visible is displayed on the blood vessel in a superimposed manner, or a form in which the filling display of the blood vessel with the highlight color and the display of the tomographic image of the blood vessel are alternately repeated.

In this case, it is preferable that the instruction mark is a dotted line-shaped frame line surrounding the blood vessel.

In the ultrasound diagnostic apparatus of the present invention, in a case where the image analysis unit detects only the blood vessel in the ultrasound image, the apparatus controller may perform control such that the highlighting unit highlights the blood vessel in the first form.

In this case, in a case where the physical quantity specified by the image analysis unit is smaller than the threshold value and is smaller than a threshold value for enlarged display smaller than the threshold value, the apparatus controller may perform control such that the highlighting unit enlarges and displays the blood vessel.

It is preferable that, in a case where the physical quantity specified by the image analysis unit is smaller than the threshold value and is greater than the threshold value for enlarged display, the apparatus controller performs control such that the highlighting unit displays an instruction mark consisting of a frame line surrounding the blood vessel, around the blood vessel in a state in which an interval depending on the threshold value for enlarged display is provided between the blood vessel and the instruction mark.

In the ultrasound diagnostic apparatus of the present invention, the apparatus controller may determine whether or not a part of the insert detected by the image analysis unit stays inside the blood vessel, and in a case where determination is made that a part of the insert stays inside the blood vessel, may perform control such that the highlighting unit continues to enlarge and display the blood vessel while a part of the insert stays inside the blood vessel.

On the other hand, the apparatus controller may determine whether or not a part of the insert detected by the image analysis unit stays inside the blood vessel, and in a case where determination is made that a part of the insert stays inside the blood vessel, may perform control that the highlighting unit stops the highlighting of the blood vessel.

In the ultrasound diagnostic apparatus of the present invention, in a case where the image analysis unit detects the blood vessel and the insert, the apparatus controller may set an effective operation region inside the ultrasound image based on a position of the blood vessel detected by the image analysis unit, may determine whether or not a distal end of the insert detected by the image analysis unit is within the effective operation region, in a case where determination is made that the distal end of the insert is within the effective operation region, may perform control such that the highlighting unit highlights the blood vessel in the second form, and in a case where determination is made that the distal end of the insert is outside the effective operation region, may perform control such that the highlighting unit highlights the blood vessel in the first form.

In this case, it is preferable that the image analysis unit estimates an insertion direction of the insert in a case where the blood vessel and the insert are detected, the apparatus controller sets the effective operation region based on the position of the blood vessel detected by the image analysis unit and the insertion direction estimated by the image analysis unit, and the highlighting unit highlights the blood vessel detected by the image analysis unit and the effective operation region set by the apparatus controller.

The ultrasound diagnostic apparatus may further comprise an input device to which identification information of an operator of the insert is input, and the apparatus controller sets a length of the effective operation region in a width direction of the ultrasound image to a length corresponding to the identification information input to the input device in setting the effective operation region.

In the ultrasound diagnostic apparatus of the present invention, in a case where the insert and a plurality of the blood vessels are detected, the image analysis unit may specify the physical quantity on each of the plurality of the blood vessels, the apparatus controller may determine whether or not each of the plurality of the blood vessels detected by the image analysis unit is at a position reachable by the insert, and the apparatus controller may perform control such that the highlighting unit highlights only the blood vessel that has the physical quantity specified by the image analysis unit smaller than the threshold value and is closest to the insert, among the blood vessels determined to be at the position reachable by the insert, in the second form.

In this case, the image analysis unit may estimate an insertion direction of the detected insert, and in determining whether or not each of the plurality of the blood vessels detected by the image analysis unit is at the position reachable by the insert, the apparatus controller may perform the determination based on the insertion direction estimated by the image analysis unit.

In the ultrasound diagnostic apparatus of the present invention, in a case where the insert is detected, the image analysis unit may analyze the ultrasound image to execute measurement processing regarding an insertion operation of the insert, and the apparatus controller may perform control such that the highlighting unit changes a display range or a display size in a case where the highlighting unit highlights the blood vessel in the second form, depending on a measurement result of the measurement processing.

In this case, it is preferable that the ultrasound diagnostic apparatus further comprises a learning unit that learns a correspondence relationship between the display range or the display size and the measurement result of the measurement processing, and the apparatus controller performs control such that the highlighting unit highlights the blood vessel in the second form with the display range or the display size derived from the correspondence relationship learned by the learning unit and the measurement result of the measurement processing.

The ultrasound diagnostic apparatus of the present invention may further comprise an input device to which identification information of an operator of the insert is input. In this case, the apparatus controller may perform control such that the highlighting unit changes a display range or a display size in a case where the highlighting unit highlights the blood vessel in the second form, depending on information regarding the operator who is identified by the identification information input to the input device.

The ultrasound diagnostic apparatus of the present invention may further comprise a storage unit that stores, as the information regarding the operator, a use history of the ultrasound diagnostic apparatus by the operator to correspond to the identification information. In this case, the apparatus controller may read out the use history corresponding to the identification information input to the input device from the storage unit and may perform control such that the highlighting unit changes a display range or a display size in a case where the highlighting unit highlights the blood vessel in the second form, depending on the read-out use history.

The ultrasound diagnostic apparatus of the present invention may further comprise an input device to which setting information regarding a display range or a display size in a case where the highlighting unit highlights the blood vessel in the second form is input. In this case, the apparatus controller may perform control such that the highlighting unit highlights the blood vessel in the second form with the display range or the display size that is indicated by the setting information input to the input device.

Identification information of an operator of the insert may be further input to the input device. In this case, it is preferable that the ultrasound diagnostic apparatus further comprises a storage unit that stores the setting information input from a certain operator in association with the identification information of the certain operator, and in a case where the identification information is input to the input device, the apparatus controller reads out the setting information associated with the input identification information among the setting information stored in the storage unit and performs control such that the highlighting unit highlights the blood vessel in the second form with the display range or the display size that is indicated by the read-out setting information.

The ultrasound diagnostic apparatus of the present invention may further comprise an ultrasound probe having the transducer array, and a processor to which the ultrasound probe is connected. In this case, the image acquisition unit may be configured with a transmission circuit that causes the transducer array to transmit the ultrasound beam toward the subject, a reception circuit that processes a signal output from the transducer array having received the ultrasound echo generated inside the subject to generate a sound ray signal, and an image generation unit that generates the ultrasound image based on the sound ray signal generated by the reception circuit, and each of the transmission circuit, the reception circuit, and the image generation unit may be provided in the ultrasound probe or the processor.

To achieve the above-described object, the present invention provides a method of controlling an ultrasound diagnostic apparatus that displays a blood vessel of a subject and an insert inserted into the blood vessel in an ultrasound image, the method comprising causing transmission of an ultrasound beam from a transducer array toward the subject and receiving an ultrasound echo generated inside the subject to acquire the ultrasound image, displaying the acquired ultrasound image on a display device, analyzing the acquired ultrasound image to detect the blood vessel and the insert in the ultrasound image, highlighting the detected blood vessel in a case where the ultrasound image is displayed on the display device, and changing a form in highlighting the blood vessel depending on a relative positional relationship between the detected blood vessel and insert.

According to the present invention, the ultrasound image is analyzed to detect the blood vessel and the insert in the ultrasound image, and the detected blood vessel is highlighted in a case where the ultrasound image is displayed on the display device. The form in highlighting the blood vessel is changed depending on the relative positional relationship between the detected blood vessel and insert. With this, it is possible to appropriately highlight the blood vessel in the ultrasound image depending on an insertion state of the insert.

DESCRIPTION OF THE PREFERRED EMBODIMENTS

Hereinafter, a plurality of specific embodiments (first embodiment to sixth embodiment) of the present invention will be described referring to the accompanying drawings. It should be noted that the embodiments described below are merely examples for ease of understanding of the present invention, and do not limit the present invention. The present invention can be changed or improved from the embodiments described below without departing from the spirit of the present invention. The present invention includes equivalents thereof.

In the following description, it is assumed that the upper and lower sides and the right and left sides of an ultrasound image are upper and lower sides and right and left sides when an operator views the ultrasound image from the front. For example, in an ultrasound image U shown in FIG. 4, an insert C is positioned upward of a blood vessel B.

<<Purpose of Ultrasound Diagnostic Apparatus of the Present Invention>>

In describing each embodiment of the present invention, the purpose of an ultrasound diagnostic apparatus of the present invention will be described.

The ultrasound diagnostic apparatus of the present invention is used in the procedure for inserting an insert, such as a puncture needle and a catheter, into a blood vessel of a subject while observing the inside of the subject, for example, an echo guided puncture method.

That is, the ultrasound diagnostic apparatus of the present invention is an apparatus that displays the blood vessel of the subject and the insert inserted into the blood vessel in an ultrasound image, and an operator of the insert appropriately observes the ultrasound image displayed by the ultrasound diagnostic apparatus during an insertion operation of the insert.

In the following description, unless otherwise specified, it is assumed that the ultrasound image is a B mode image (tomographic image) regarding a tissue inside the subject.

Hereinafter, although a case where the insert is a catheter with a puncture needle will be described as an example, the ultrasound diagnostic apparatus of the present invention can also be applied to a case where an insert other than the catheter with a puncture needle is inserted into the blood vessel. Here, the insert extends linearly, and can puncture a body surface and a vascular wall of the subject.

First Embodiment

Figure 1:
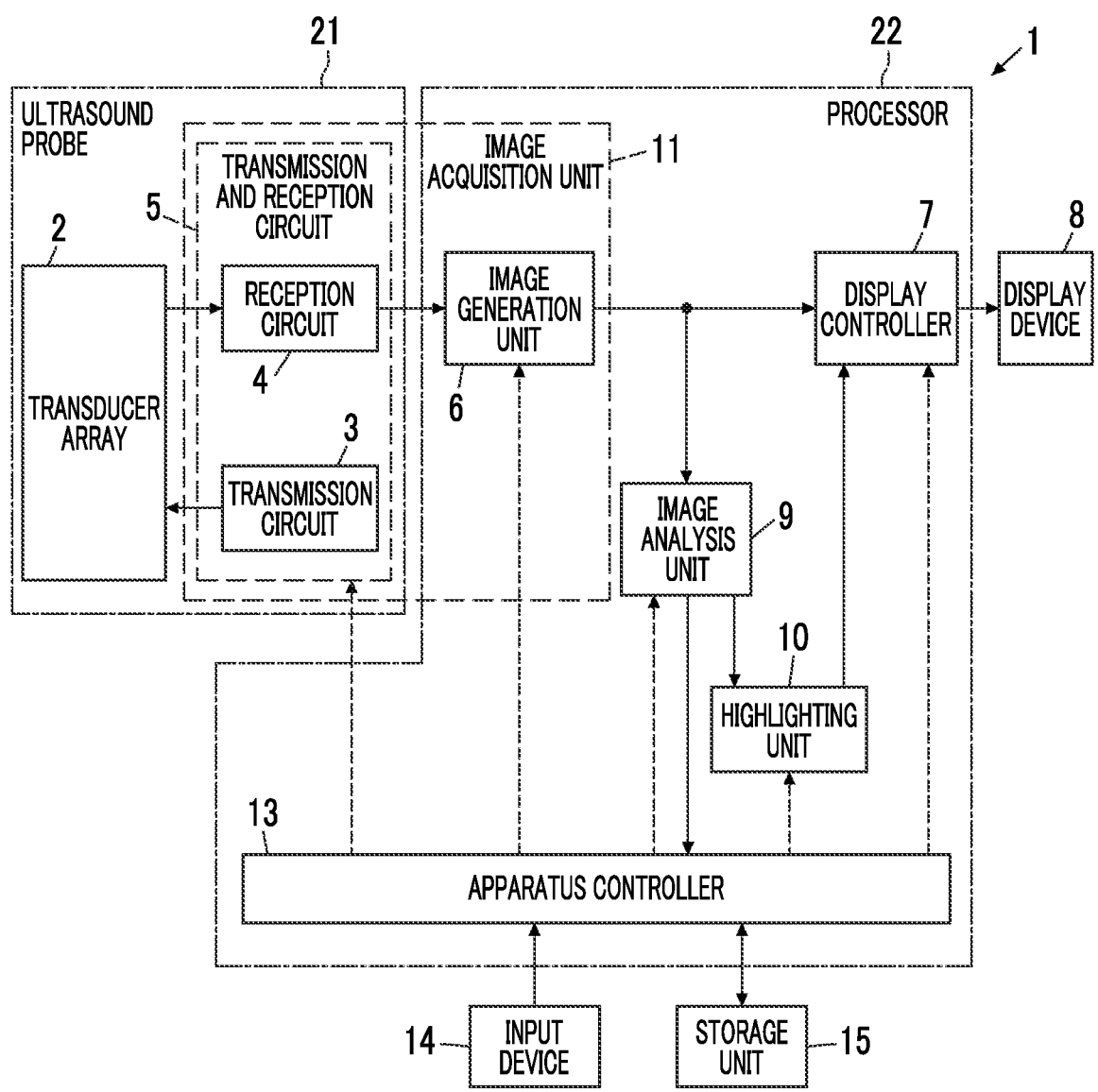
FIG. 1 is a block diagram showing the configuration of an ultrasound diagnostic apparatus according to a first embodiment of the present invention.

As shown in FIG. 1, an ultrasound diagnostic apparatus (hereinafter, referred to as an ultrasound diagnostic apparatus 1) according to the first embodiment of the present invention has an ultrasound probe 21 that comprises a transducer array 2, and a processor 22 that is connected to the ultrasound probe 21. Each of a transmission circuit 3 and a reception circuit 4 is connected to the transducer array 2. The transmission circuit 3 and the reception circuit 4 configure a transmission and reception circuit 5 and are included in the ultrasound probe 21 in the configuration shown in FIG. 1. An image generation unit 6 is connected to the reception circuit 4, a display controller 7 is connected to the image generation unit 6, and a display device 8 is connected to the display controller 7.

An image analysis unit 9 is connected to the image generation unit 6, a highlighting unit 10 is connected to the image analysis unit 9, and the display controller 7 is connected to the highlighting unit 10. An apparatus controller 13 is connected to each of the transmission and reception circuit 5, the image generation unit 6, the display controller 7, the image analysis unit 9, and the highlighting unit 10, and an input device 14 and a storage unit 15 are connected to the apparatus controller 13. The apparatus controller 13 and the storage unit 15 are connected in a state in which information can be transferred therebetween.

In the configuration of FIG. 1, the image generation unit 6, the display controller 7, the image analysis unit 9, the highlighting unit 10, and the apparatus controller 13 are provided (mounted) in the processor 22. The transmission and reception circuit 5 (that is, the transmission circuit 3 and the reception circuit 4) of the ultrasound probe 21 and the image generation unit 6 of the processor 22 cooperate with each other and configure an image acquisition unit 11 that acquires an ultrasound image.

The transducer array 2 has a plurality of transducers arranged in a one-dimensional or two-dimensional manner. A plurality of transducers may be arranged linearly like a linear ultrasound probe 21 or may be arranged in a curved manner like a convex or sector ultrasound probe 21. Each of a plurality of transducers transmits an ultrasonic wave in response to a drive signal supplied from the transmission circuit 3, receives an ultrasound echo generated inside the subject, and outputs an electric signal based on the ultrasound echo. Each transducer is configured by forming electrodes at both ends of a piezoelectric body consisting of, for example, piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission circuit 3 causes the transducer array 2 to transmit an ultrasound beam toward the subject. Specifically, the transmission circuit 3 includes, for example, a plurality of pulse generators, and adjusts a delay amount of each drive signal to a plurality of transducers of the transducer array 2 based on a transmission delay pattern selected in response to a control signal from the apparatus controller 13 and supplies the drive signal to the drive signals to a plurality of transducers. Each drive signal is a pulsed or continuous-wave voltage signal, and in a case where the drive signal is applied to the electrodes of each transducer of the transducer array 2, the piezoelectric body expands and contracts. As a result, a pulsed or continuous-wave ultrasonic wave is generated from each transducer, and an ultrasound beam is formed from a combined wave of the ultrasonic waves.

The transmitted ultrasound beam is reflected by, for example, each part (for example, an organ and a blood vessel) inside the subject and appliance disposed inside the subject. With this, an ultrasound echo is generated and propagates inside the subject toward the transducer array 2, and is finally received by a plurality of transducers of the transducer array 2. In this case, each transducer expands and contracts with the reception of the ultrasound echo to generate an electric signal, and outputs the electric signal to the reception circuit 4.

Figure 2:
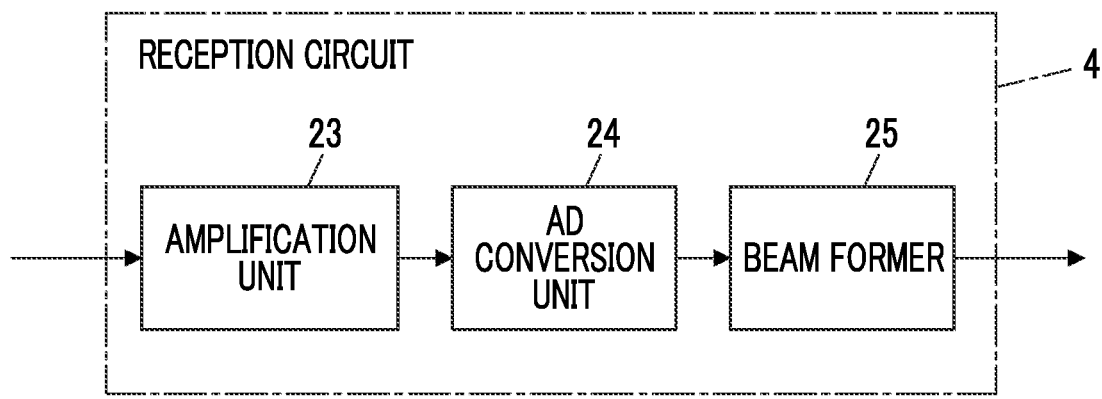
FIG. 2 is a block diagram showing the internal configuration of a reception circuit according to the first embodiment of the present invention.

The reception circuit 4 executes predetermined processing on a signal (strictly, an analog electric signal) output from the transducer array 2 in response to a control signal from the apparatus controller 13 to generate a sound ray signal. For example, as shown in FIG. 2, the reception circuit 4 has a configuration in which an amplification unit 23, an analog-digital (AD) conversion unit 24, and a beam former 25 are connected in series.

The amplification unit 23 amplifies a signal output from each of a plurality of transducers of the transducer array 2 and transmits the amplified signal to the AD conversion unit 24. The AD conversion unit 24 converts the amplified signal into digital reception data and transmits each piece of converted reception data to the beam former 25. The beam former 25 executes reception focus processing of giving a delay to each piece of reception data converted by the AD conversion unit 24 conforming to a sound speed or a distribution of a sound speed set based on a reception delay pattern selected in response to a control signal from the apparatus controller 13 and performing addition. With the reception focus processing, each piece of reception data converted by the AD conversion unit 24 is subjected to phasing addition, and a sound ray signal in which a focus of the ultrasound echo is narrowed is acquired.

Figure 3:
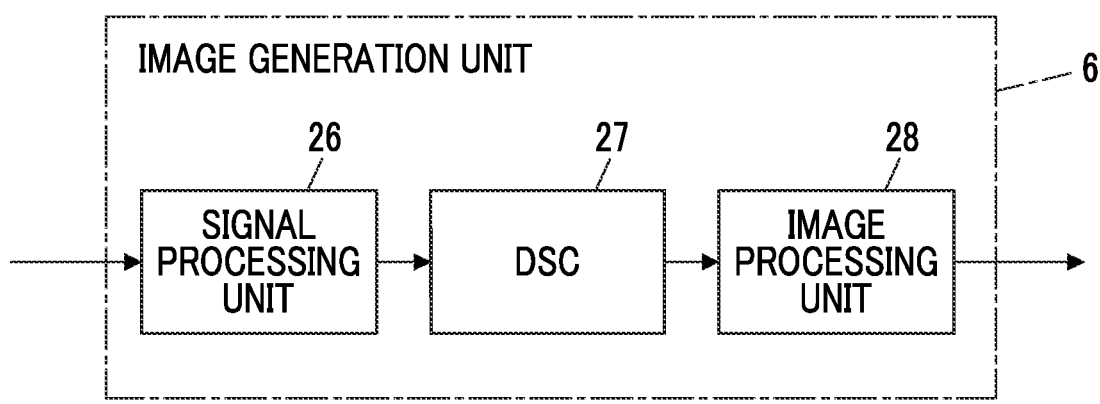
FIG. 3 is a block diagram showing the internal configuration image generation unit according to the first embodiment of the present invention.

The image generation unit 6 generates an ultrasound image based on the sound ray signal generated by the reception circuit 4, and as shown in FIG. 3, has a configuration in which a signal processing unit 26, a digital scan converter (DSC) 27, and an image processing unit 28 are sequentially connected in series.

The signal processing unit 26 performs correction of attenuation on the sound ray signal generated by the reception circuit 4 due to a distance depending on a depth of a reflection position of the ultrasonic wave, and then, executes envelope detection processing, thereby generating a B mode image signal indicating an ultrasound image.

The DSC 27 converts (raster-converts) the B mode image signal generated by the signal processing unit 26 into an image signal conforming to a normal television signal scanning system.

The image processing unit 28 executes various kinds of necessary image processing, such as gradation processing, on the B mode image signal input from the DSC 27, and then, outputs the B mode image signal to the display controller 7 and the image analysis unit 9. The B mode image signal subjected to the image processing by the image processing unit 28 corresponds to an ultrasound image.

The apparatus controller 13 performs control such that the image acquisition unit 11 configured with the transmission and reception circuit 5 and the image generation unit 6 continuously acquires ultrasound images at a given frame rate multiple times in an acquisition period of the ultrasound image.

Figure 4:
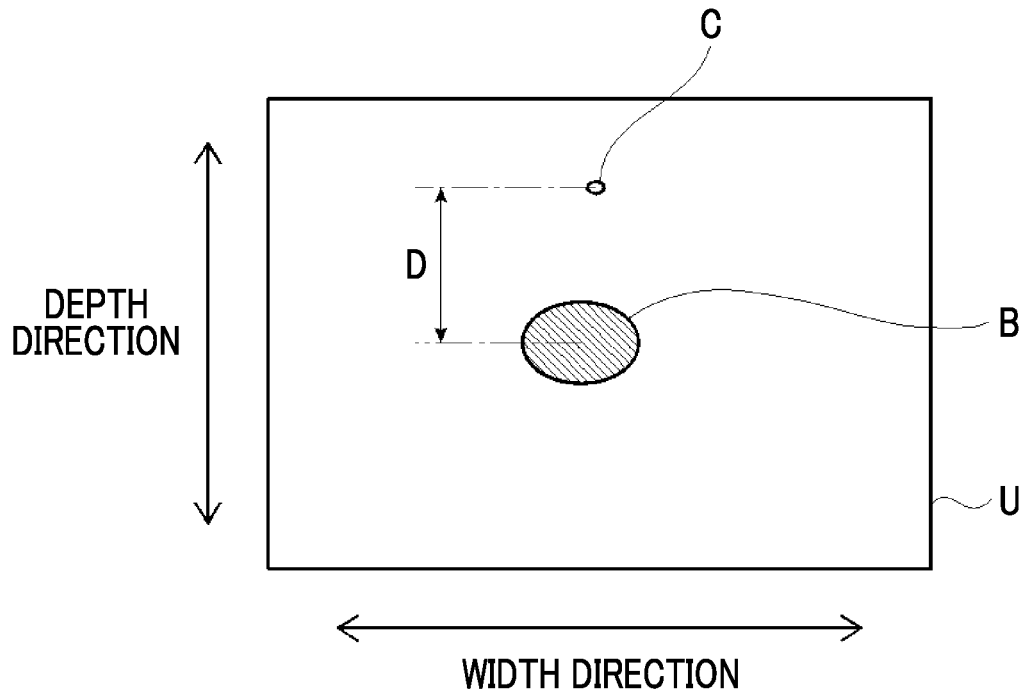
FIG. 4 is a schematic view of an ultrasound image that is displayed on a display device by the ultrasound diagnostic apparatus according to the first embodiment of the present invention.

The display controller 7 executes predetermined processing on the ultrasound image generated by the image generation unit 6 (in other words, the ultrasound image acquired by the image acquisition unit 11) and displays the ultrasound image on the display device 8 under the control of the apparatus controller 13. As shown in FIG. 4, the ultrasound image (hereinafter, referred to as an ultrasound image U) displayed on the display device 8 is developed in a depth direction and a width direction. Here, the width direction of the ultrasound image U is a direction in which a plurality of scanning lines configuring the ultrasound image U are arranged. The depth direction of the ultrasound image U is a direction in which the scanning lines extend. Each portion in the ultrasound image U is displayed at a position depending on a distance (depth) from a body surface of the subject with which the ultrasound probe 21 is brought into contact, in the depth direction.

A transverse section of the blood vessel B and a transverse section of a distal end part of the insert C that are observed by a minor axis method (crossover method) are rendered in the ultrasound image U of FIG. 4, and of these, the transverse section of the blood vessel B is highlighted in a first form described below. Here, the transverse section of the blood vessel B is a cut section of the blood vessel B along a plane perpendicular to an extension direction of the blood vessel B, and the transverse section of the distal end part of the insert C is a cut section of the distal end part of the insert C along the plane perpendicular to the extension direction of the insert C.

The display device 8 is a device that displays the ultrasound image U and the like under the control of the display controller 7, and includes, for example, a liquid crystal display (LCD) or an organic electroluminescence display (organic EL display).

The image analysis unit 9 detects the blood vessel B and the insert C in the ultrasound image U by analyzing the ultrasound image generated by the image generation unit 6 (in other words, the ultrasound image acquired by the image acquisition unit 11). Here, the image analysis unit 9 can detect the blood vessel B and the insert C in the ultrasound image U using a known algorithm. For example, the image analysis unit 9 can store typical pattern data of the blood vessel B and the insert C as templates in advance, can calculate similarity to the pattern data while searching the ultrasound image U with the templates, and can regard that the blood vessel B and the insert C are at locations where the similarity is equal to or greater than a predetermined value and is the maximum.

In the calculation of the similarity, in addition to simple template matching, for example, a machine learning method described in Csurka et al.: Visual Categorization with Bags of Keypoints, Proc. of ECCV Workshop on Statistical Learning in Computer Vision, pp. 59-74 (2004) or a general image recognition method using deep learning described in Krizhevsk et al.: ImageNet Classification with Deep Convolutional Neural Networks, Advances in Neural Information Processing Systems 25, pp. 1106-1114 (2012) can be used.

The image analysis unit 9 can specify a relative positional relationship between the blood vessel B and the insert C detected in the above-described manner, and specifically, as shown in FIG. 4, can measure and specify a distance D between the distal end of the insert C and the blood vessel B detected in the above-described manner. The distance D is a physical quantity representing the relative positional relationship between the blood vessel B and the insert C detected in the above-described manner, and for example, the image analysis unit 9 can measure, as the distance D, the shortest distance between the center position of the distal end of the insert C and the center position of the blood vessel B.

The highlighting unit 10 highlights the blood vessel B detected by the image analysis unit 9 in a case where the ultrasound image U is displayed on the display device 8. As the blood vessel B in the ultrasound image U is highlighted by the highlighting unit 10 in this way, the blood vessel B into which the insert C is inserted is easily found in the ultrasound image U, and it is possible to improve operation accuracy in a case where the operator inserts the insert C into the blood vessel B.

Figure 5:
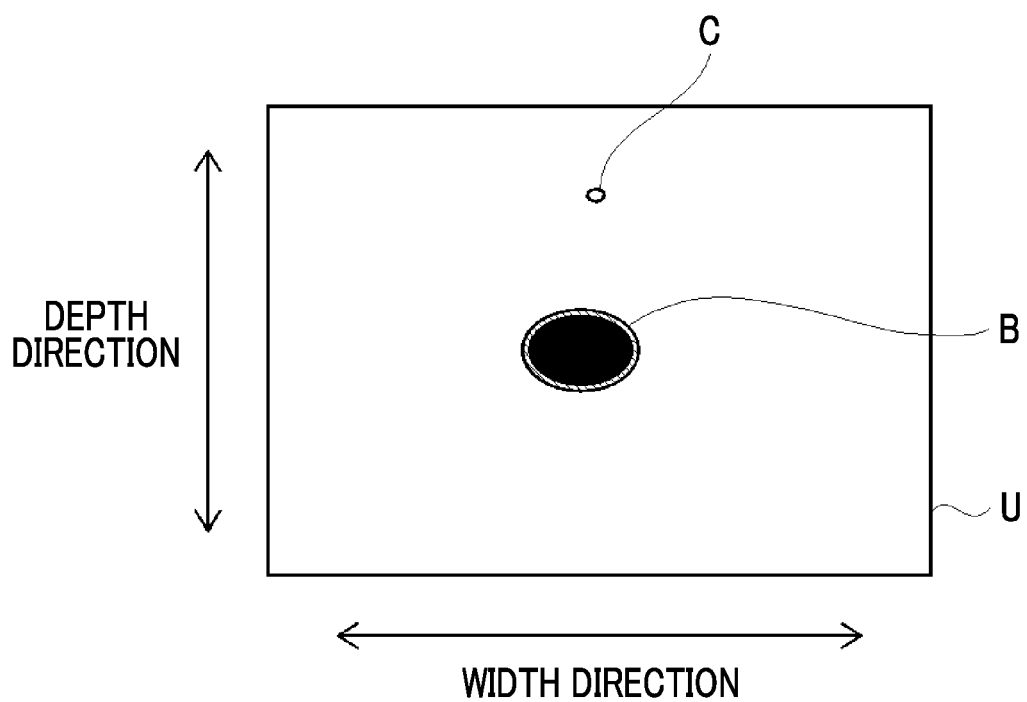
FIG. 5 is a diagram showing an example where a blood vessel in the ultrasound image is highlighted in a first form in the first embodiment of the present invention (first view).
Figure 6:
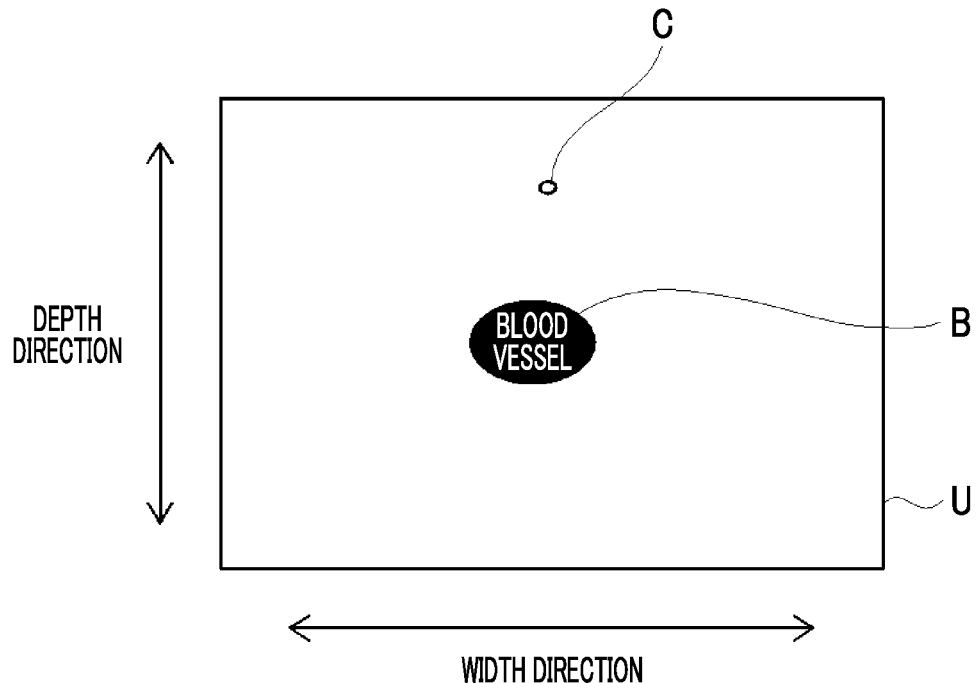
FIG. 6 is a diagram showing an example where the blood vessel in the ultrasound image is highlighted in the first form in the first embodiment of the present invention (second view).
Figure 7:
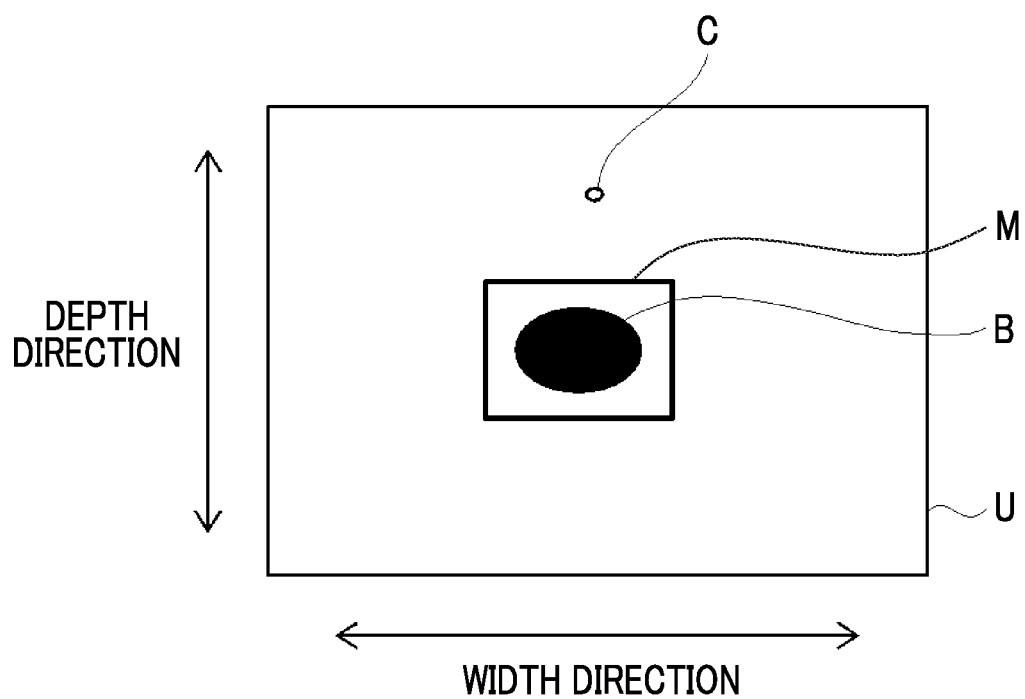
FIG. 7 is a diagram showing an example where the blood vessel in the ultrasound image is highlighted in the first form in the first embodiment of the present invention (third view).

A form in a case where the highlighting unit 10 highlights the blood vessel B includes a first form and a second form and is switched therebetween. The first form is a form giving priority to the visibility (ease of finding) of the blood vessel B, and specific examples of the first form include a form in which the blood vessel B in the ultrasound image U is displayed to be filled with a highlight color as shown in FIG. 4, a form in which the contour of the blood vessel B is displayed in the highlight color as shown in FIG. 5, a form in which a character string is displayed at a position overlapping the blood vessel B as shown in FIG. 6, and a form in which an instruction mark M (for example, a bounding box and an arrow) of the blood vessel B is displayed around the blood vessel B as shown in FIG. 7.

In the first embodiment, as the first form, any one of the above-described three forms can be employed. Alternatively, a form in which some of the three forms are combined, for example, a form in which the instruction mark M is displayed at the same time while filling the blood vessel B with the highlight color may be employed.

Hereinafter, a case where a form in which the blood vessel B is filled with the highlight color and highlighted is employed as the first form will be described as an example.

It is desirable that the highlight color is a color that is easily visible by the operator, and more preferably, may be a color with high saturation, such as yellow, orange, light green, light blue, or pink. A case where the blood vessel B is displayed to be filled with the highlight color refers to that the color of a display region of the blood vessel B in the ultrasound image U is set as the highlight color and the alpha channel (transmittance) of the display region is set to a value at which a tomographic image (B mode image) of the blood vessel B is not visible.

The second form is a form different from the first form and is a form in which the blood vessel B is highlighted while avoiding interference with the blood vessel B detected by the image analysis unit 9. Here, "interference with the blood vessel B" means that the whole or a part of the vascular wall of the blood vessel B and the tomographic image (B mode image) inside the blood vessel is not visible, and "the display form of avoiding interference with the blood vessel B" means a form in which the vascular wall of the blood vessel B and the tomographic image (B mode image) inside the blood vessel B are displayed in a state in which the whole thereof is viewed. The "display form of avoiding interference with the blood vessel B" also includes a display form in which display is performed with temporary interference with the blood vessel B or another object is displayed to overlap the blood vessel B, but the whole of the vascular wall of the blood vessel B and the tomographic image inside the blood vessel is visible (that is, a display form that allows partial interference).

Figure 8:
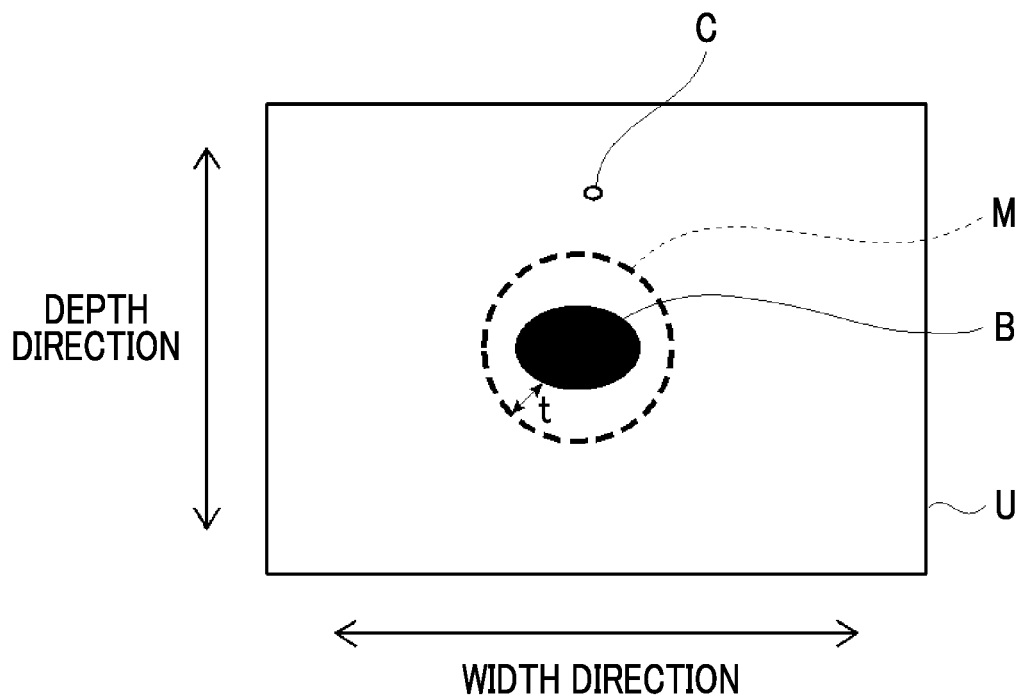
FIG. 8 is a diagram showing an example where the blood vessel in the ultrasound image is highlighted in a second form in the first embodiment of the present invention (first view).
Figure 9:
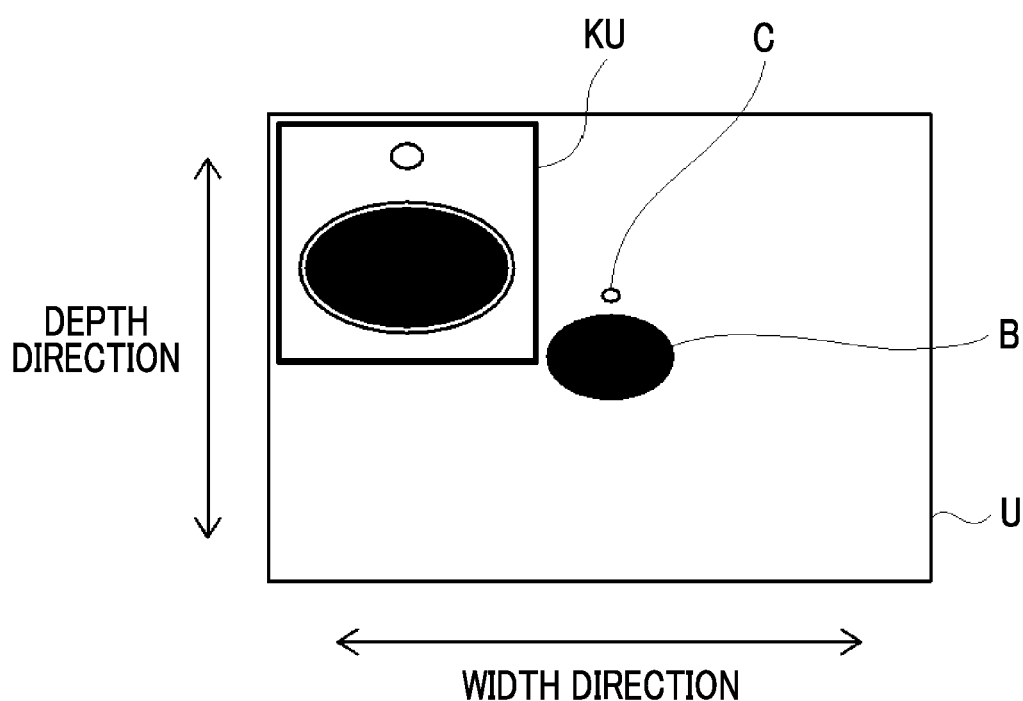
FIG. 9 is a diagram showing an example where the blood vessel in the ultrasound image is highlighted in the second form in the first embodiment of the present invention (second view).
Figure 10:
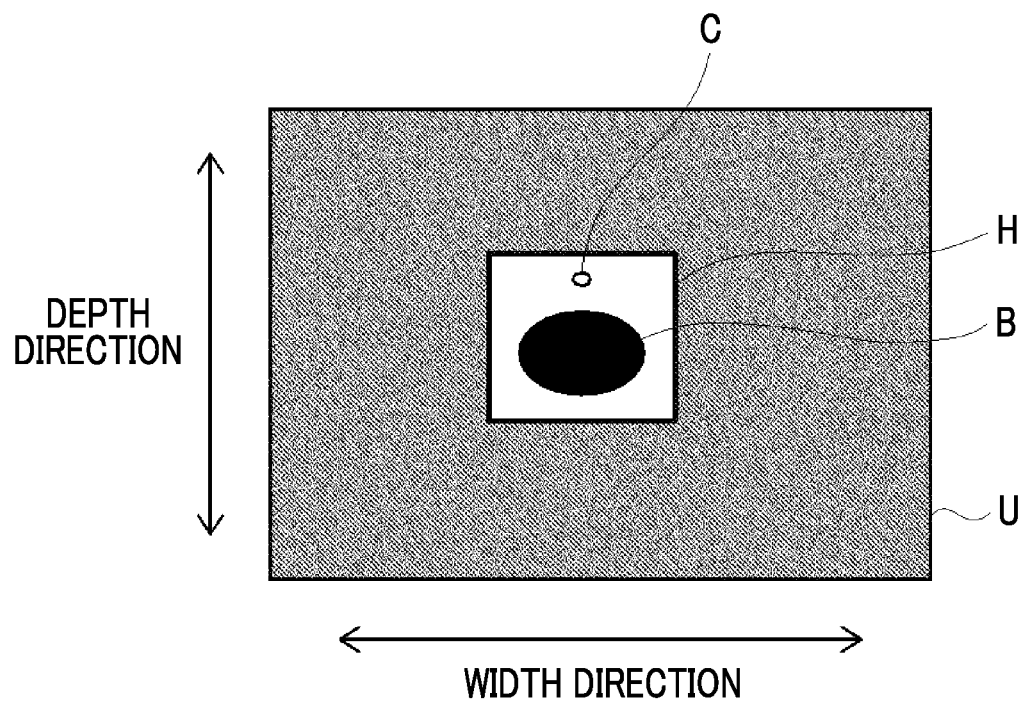
FIG. 10 is a diagram showing an example where the blood vessel in the ultrasound image is highlighted in the second form in the first embodiment of the present invention (third view).

Specific examples of the second form include a form in which an instruction mark M of the blood vessel B is displayed around the blood vessel B while being separated from the blood vessel B in the ultrasound image U as shown in FIG. 8, a form in which the blood vessel B is enlarged and displayed as shown in FIG. 9, and a form in which the blood vessel B in the ultrasound image U is displayed with brightness brighter than the vicinity as shown in FIG. 10.

Figure 11:
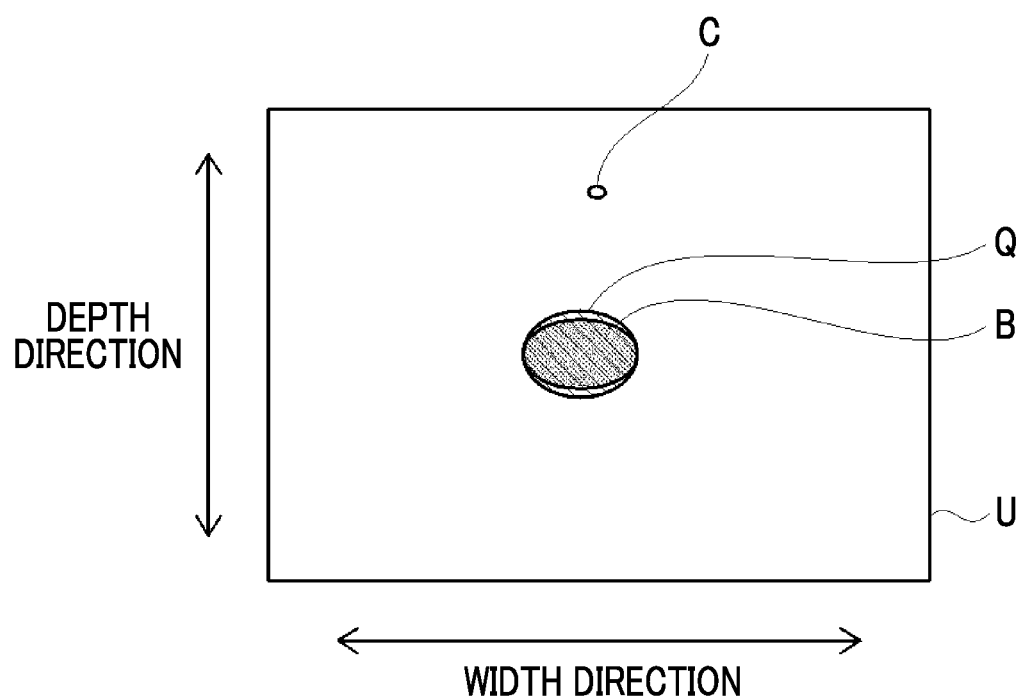
FIG. 11 is a diagram showing an example where the blood vessel in the ultrasound image is highlighted in the second form in the first embodiment of the present invention (fourth view).
Figure 12:
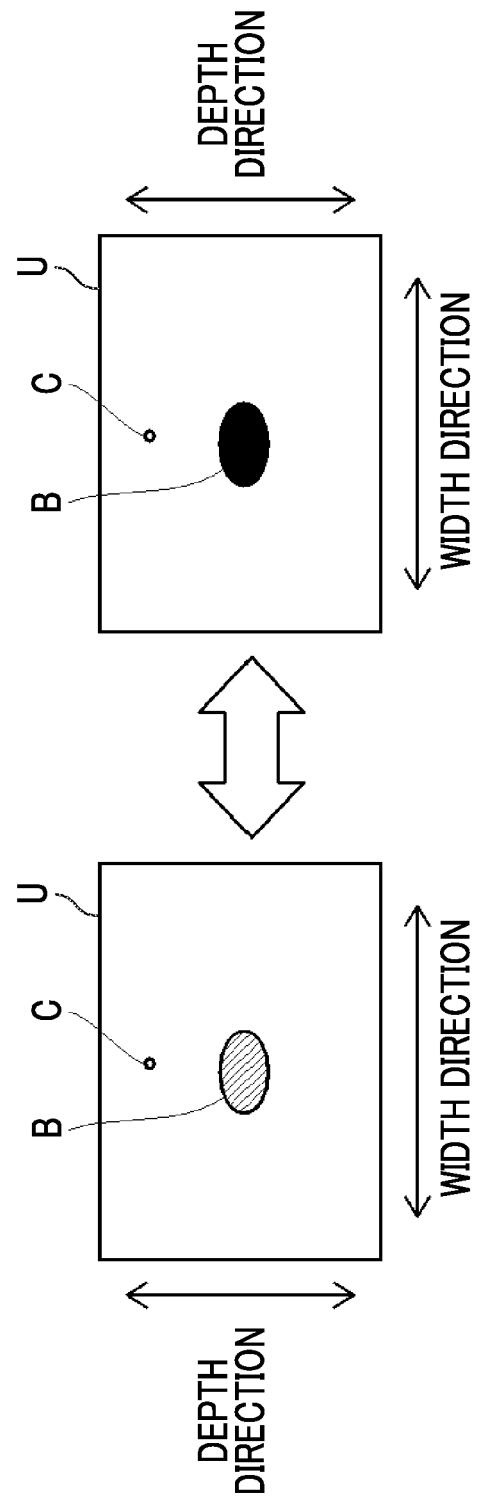
FIG. 12 is a diagram showing an example where the blood vessel in the ultrasound image is highlighted in the second form in the first embodiment of the present invention (fifth view).

Specific examples of the second form further include, in addition to the three forms described above, a form in which a filling layer Q of the highlight color set to have transmittance such that the tomographic image (B mode image) of the blood vessel B is visible is displayed on the blood vessel B in a superimposed manner as shown in FIG. 11, and a form in which the filling display of the blood vessel B with the highlight color and the display of the tomographic image of the blood vessel B are alternately repeated as shown in FIG. 12.

In the form (hereinafter, referred to as an instruction mark display form) in which the instruction mark M is displayed around the blood vessel B, a frame line surrounding the blood vessel B, such as a bounding box and a circle (including an ellipse), corner marks disposed at four corners of a rectangle surrounding the blood vessel B, and a form in which an arrow or the like disposed near the blood vessel B is displayed in a set color, such as the highlight color, not to interfere with the blood vessel B.

in the form (hereinafter, referred to as an enlarged display form) in which the blood vessel B is enlarged and displayed, an enlarged display image KU obtained by enlarging and displaying the blood vessel B in the ultrasound image U at a predetermined magnification is displayed on the ultrasound image U in a superimposed manner. Here, the enlarged display image KU is obtained by rendering the whole of the blood vessel B of the ultrasound image U. For this reason, even in a case where the blood vessel B is displayed at a position deviated from a region where the enlarged display image KU is displayed in the ultrasound image U or even in a case where the enlarged display image KU is displayed to overlap the display region of the blood vessel B, it is possible to highlight the blood vessel B of the ultrasound image U while avoiding interference with the blood vessel B.

In displaying the enlarged display image KU to overlap the display region of the blood vessel B, full screen enlargement may be made in which the aspect of the enlarged display image KU coincides with the aspect of the ultrasound image U as an original image or quasi-full screen enlargement may be made in which the aspects of both images do not coincide with each other.

Though not particularly shown, the screen of the display device 8 may be divided into two divided screens, the enlarged display image KU may be displayed on one divided screen, and the ultrasound image U as an original image may be displayed on the other divided screen.

In the form (hereinafter, referred to as a spotlight display form) in which the blood vessel B is displayed with brightness brighter than the vicinity), in the ultrasound image U, the brightness of the display region of the blood vessel B increases higher than the brightness of the vicinity or the brightness of the vicinity decreases lower (is made darker) than the brightness of the display region of the blood vessel B. Here, in a spotlight display region H having the brightness brighter than the vicinity in the ultrasound image U, as shown in FIG. 10, the whole of the blood vessel B of the ultrasound image U is rendered. For this reason, even in the above-described spotlight display form, it is possible to highlight the blood vessel B of the ultrasound image U while avoiding interference of the blood vessel B.

In the form in which the filling layer Q of the highlight color is displayed on the blood vessel B in a superimposed manner, as shown in FIG. 11, the filling layer Q having the same shape and size as the detected blood vessel B is displayed to overlap a position directly above the blood vessel B to highlight the blood vessel B. Here, the filling layer Q is an object where a display color is the highlight color and an alpha channel (transmittance) is set to transparency or semitransparency.

In the form in which the filling display of the blood vessel B with the highlight color and the display of the tomographic image of the blood vessel B are alternately repeated, a state in which the detected blood vessel B is displayed in the highlight color (a state shown on the left side of FIG. 12) and a state in which the detected blood vessel B is displayed in a color in a normal B mode image (a state shown on the right side of FIG. 12) are alternately switched, such that the blood vessel B is highlighted like blinking in a pseudo manner.

As the second form, any one of the above-described five forms can be employed. Alternatively, a form in which some of the above-described five forms are combined, for example, a form in which the blood vessel B is enlarged and displayed along with the instruction mark M or a form in which the blood vessel B is enlarged and displayed with brightness brighter than the vicinity may be employed.

In the first embodiment, in a case where the distance D between the blood vessel B and the insert C in the ultrasound image U specified by the image analysis unit 9 is smaller than a threshold value described below, the highlighting unit 10 highlights the blood vessel B in the instruction mark display form. In this case, as shown in FIG. 8, as the instruction mark M, a dotted line-shaped frame line surrounding the blood vessel B in the ultrasound image U is displayed. The frame line is a dotted line, whereby it is possible to suppress a state in which the distal end of the insert C is hardly viewed in a case where the insert C is inserted near the frame line.

The frame line forming the instruction mark M is not limited to the dotted line, and may be a solid line.

In a case where the above-described distance D is further shortened and is smaller than a threshold value for enlarged display described below, the highlighting unit 10 highlights the blood vessel B in the enlarged display form. In this case, in the enlarged display image KU, as shown in FIG. 9, the blood vessel B into which the insert C is inserted and the distal end of the insert C positioned near the blood vessel B are included.

The apparatus controller 13 performs control of each unit of the ultrasound diagnostic apparatus 1 based on a program stored in advance in the storage unit 15 or the like, information input from the operator through the input device 14, and the like.

The apparatus controller 13 performs control such that the highlighting unit 10 changes the form in highlighting the blood vessel B depending on the relative positional relationship between the blood vessel B and the insert C in the ultrasound image U detected by the image analysis unit 9.

In more detail, in a case where the image analysis unit 9 detects only the blood vessel B in the ultrasound image U and does not detect the insert C, the apparatus controller 13 performs control such that the highlighting unit 10 highlights the blood vessel B in the first form. In this case, the blood vessel B in the ultrasound image U is displayed to be filled with the highlight color.

In a case where the image analysis unit 9 detects both the blood vessel B and the insert C in the ultrasound image U, and the distance D between the blood vessel B and the insert C specified by the image analysis unit 9 is greater than a threshold value, the apparatus controller 13 performs control such that the highlighting unit 10 continuously highlights the blood vessel B in the first form. Here, the threshold value is a predetermined value as a criterion for determining a need for switching a highlighting form, and is stored in, for example, the storage unit 15.

That is, in an initial stage where the insert C is inserted into the subject, the distal end of the insert C is at a position separated from the blood vessel B. Thus, the blood vessel B is highlighted in the first form focusing on the visibility (ease of finding) of the blood vessel B in the ultrasound image U. With this, the operator can easily find out the blood vessel B into which the insert C is inserted, in the ultrasound image U.

On the other hand, in a case where the above-described distance D is smaller than the threshold value, the apparatus controller 13 performs control such that the highlighting unit 10 highlights the blood vessel B in the second form. That is, in a case where the distal end of the insert C is positioned near the blood vessel B, the blood vessel B is highlighted while avoiding interference with the blood vessel B, and the vascular wall of the blood vessel B and movement thereof are easily visible by the operator. With this, the operator can bring the distal end of the insert C closer to the blood vessel B while clearly confirming both the blood vessel B and the insert C.

In a case where the distance D is equal to the threshold value, the blood vessel B may be highlighted in the first form or the blood vessel B may be highlighted in the second form.

In a case where the above-described distance D is smaller than the threshold value and is greater than the threshold value for enlarged display, the apparatus controller 13 performs control such that the highlighting unit 10 highlights the blood vessel B in the instruction mark display form as the second form. On the other hand, in a case where the above-described distance D is smaller than the threshold value and is smaller than the threshold value for enlarged display, the apparatus controller 13 performs control such that the highlighting unit 10 highlights the blood vessel B in the enlarged display form as the second form. Here, the threshold value for enlarged display is a predetermined value as a determination criterion in switching the highlighting form from the instruction mark display form to the enlarged display form, is smaller than the above-described threshold value, and is stored in, for example, the storage unit 15.

In a case where the instruction mark display form is employed as the second form, as shown in FIG. 8, the apparatus controller 13 performs control such that the highlighting unit 10 displays the instruction mark M consisting of the frame line (strictly, a circular frame) surrounding the blood vessel B in the ultrasound image U, around the blood vessel B in a state in which an interval t depending on the above-described threshold value for enlarged display is provided between the blood vessel B and the instruction mark M. That is, a diameter of the instruction mark M consisting of the circular frame is a length reflecting the threshold value for enlarged display, and the instruction mark M is displayed near the blood vessel B in the ultrasound image U, whereby it is possible to visualize the threshold value for enlarged display. With this, the operator can recognize that the highlighting form is switched to the enlarged display form when the distal end of the insert C approaches the instruction mark M.

In a case where the enlarged display form is employed as the second form, as shown in FIG. 9, the apparatus controller 13 performs control such that the highlighting unit 10 displays the enlarged display image KU including the blood vessel B and the insert C in the ultrasound image U. In the enlarged display image KU, the vascular wall of the blood vessel B and the B mode image inside the blood vessel B are enlarged and displayed. That is, when the distal end of the insert C reaches the nearest position to the blood vessel B, the blood vessel B is highlighted to be more easily viewed. Thus, the vascular wall of the blood vessel B and the movement of the vascular wall are easily visible to the operator. With this, the operator can operate the insert C such that the distal end of the insert C satisfactorily passes through the vascular wall of the blood vessel B.

As described above, until the insert C is inserted into the subject to a certain extent, the blood vessel B in the ultrasound image U is highlighted in the first form, whereby it is possible to easily find the blood vessel B into which the insert C is inserted. On the other hand, in a period immediately before the distal end of the insert C enters the blood vessel B after reaching near the blood vessel B, the blood vessel B (in particular, the vascular wall) is hardly viewed in the first form. Thus, the highlighting form is switched to the second form for avoiding interference with the blood vessel B to highlight the blood vessel B. With this, since the vascular wall of the blood vessel B can be clearly confirmed, the operator can make the distal end of the insert C appropriately enter the blood vessel B.

The input device 14 is provided for the operator to perform an input operation, and can be configured with, for example, a keyboard, a mouse, a track ball, a touch pad, and a touch panel. For example, identification information of the operator is input to the input device 14. Examples of the identification information of the operator include biological information, such as a fingerprint, a voiceprint, and a retina pattern, in addition to character string information, such as a name and an identification ID of a person to be identified. In a case where the biological information is input as the identification information, the input device 14 may comprise known biological information acquisition equipment starting from a scanner or the like.

Setting information regarding a display range or a display size in a case where the highlighting unit 10 highlights the blood vessel B in the second form is input to the input device 14. The setting information corresponds to, for example, contents set by the operator regarding the display range or the display size in a case where the highlighting unit 10 highlights the blood vessel B in the enlarged display form. Here, the display range means a range in the ultrasound image U that is enlarged and displayed in the enlarged display image KU. The display size means the size of the enlarged display image KU, and in other words, corresponds to a magnification in the enlarged display image KU.

In a case where the blood vessel B is highlighted in the instruction mark display form, the size of the instruction mark M may be set as the display size, and in a case where the blood vessel B is highlighted in the spotlight display form, the range of the spotlight display region H may be set as the display range. Then, the set contents can be input as the setting information to the input device 14.

Then, in a case where the setting information is input to the input device 14, the apparatus controller 13 performs control such that the highlighting unit 10 highlights the blood vessel B in the second form with the display range or the display size indicated by the input setting information. In this way, in the first embodiment, the display range and the display size in highlighting the blood vessel B in the second form can be changed (adjusted) for each operator conforming to operator's preference.

The storage unit 15 stores a control program of the ultrasound diagnostic apparatus 1 and various kinds of information, and a recording medium, such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), an secure digital card (SD card), and a universal serial bus memory (USB memory), a server computer, or the like can be used.

The information stored in the storage unit 15 includes the threshold value and the threshold value for enlarged display described above. The storage unit 15 stores the above-described setting information input from a certain operator through the input device 14 in association with the identification information of the certain operator. The setting information stored in the storage unit 15 is read out by the apparatus controller 13 in a case where the apparatus controller 13 causes the highlighting unit 10 to highlight the blood vessel B in the second form.

Specifically, for example, in a case where the identification information of the operator is input to the input device 14 before ultrasound image acquisition starts, the apparatus controller 13 reads out the setting information associated with the input identification information among the setting information stored in the storage unit 15. Then, the apparatus controller 13 performs control such that the highlighting unit 10 highlights the blood vessel with the display range or the display size indicated by the read-out setting information in highlighting the blood vessel B in the second form.

As above, the display range or the display size set by the operator are stored as the setting information in the storage unit 15, whereby, when the ultrasound image U is highlighted to the same operator later, it is possible to highlight the blood vessel B with the display range or the display size set by the operator.

Incidentally, the processor 22 in which the image generation unit 6, the display controller 7, the image analysis unit 9, the highlighting unit 10, and the apparatus controller 13 described above is configured with, for example, a central processing unit (CPU) and a control program causing the CPU to execute various kinds of processing. The present invention is not limited thereto, and the processor 22 may be configured using a field programmable gate array (FPGA), a digital signal processor (DSP), an application specific integrated circuit (ASIC), a graphics processing unit (GPU), or other integrated circuits (ICs), or may be configured by combining such ICs.

The image generation unit 6, the display controller 7, the image analysis unit 9, the highlighting unit 10, and the apparatus controller 13 provided in the processor 22 may be configured to be partially or wholly integrated into one CPU or the like.

The processor 22 may be mounted in, for example, a stationary type apparatus or may be mounted in a portable type apparatus, such as a notebook type personal computer (PC), a smartphone, or a tablet terminal.

Figure 13:
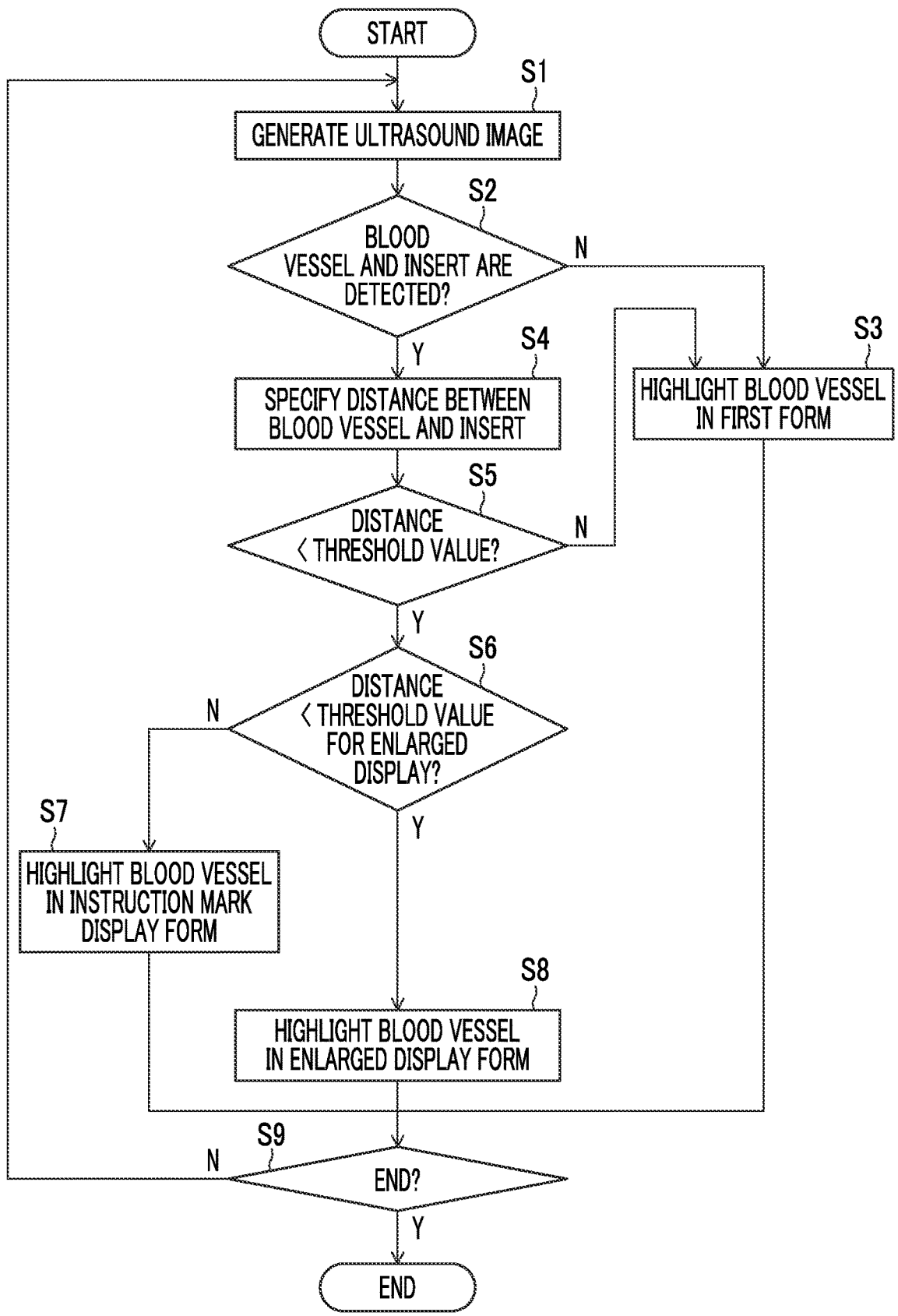
FIG. 13 is a flowchart illustrating the operation of the ultrasound diagnostic apparatus according to the first embodiment of the present invention.

Next, the operation of the ultrasound diagnostic apparatus 1 according to the first embodiment will be described in detail referring to a flowchart shown in FIG. 13.

In a display flow of an ultrasound image by the ultrasound diagnostic apparatus 1, Step S1 is executed, and in Step S1, the ultrasound image U is generated. Specifically, first, the ultrasound probe 21 is brought into contact with the body surface of the subject, an ultrasound beam is transmitted from each of a plurality of transducers of the transducer array 2 into the subject in response to the drive signals from the transmission circuit 3, and a reception signal is output from each transducer that receives the ultrasound echo, to the reception circuit 4 subject. Next, the reception signal received by the reception circuit 4 is amplified by the amplification unit 23, is AD-converted by the AD conversion unit 24, and then, is subjected to phasing addition by the beam former 25. As a result, a sound ray signal is generated. The sound ray signal is subjected to the envelope detection processing by the signal processing unit 26 in the image generation unit 6 to become a B mode image signal, and the B mode image signal is output to the display controller 7 through the DSC 27 and the image processing unit 28. With this, an ultrasound image U is generated (in other words, the ultrasound image U is acquired). The ultrasound image U is displayed on the display device 8 under the control of the display controller 7.

Hereinafter, description will be provided on an assumption that the ultrasound image U generated in Step S1 includes at least the blood vessel B of the subject.

In next Step S2, the image analysis unit 9 detects the blood vessel B and the insert C in the ultrasound image U by analyzing the generated ultrasound image U. In this case, the image analysis unit 9 can detect the blood vessel B and the insert C in the ultrasound image U by applying, for example, a known algorithm, such as template matching, a machine learning method, or a general image recognition method using deep learning.

In a case where the operator does not yet insert the insert C into the subject at the time of execution of Step S2, of course, the insert C is not detected in the ultrasound image U, and only the blood vessel B is detected. In this case, Step S3 is executed, and in Step S3, the apparatus controller 13 performs control such that the highlighting unit 10 highlights the blood vessel B in the ultrasound image U in the first form. With this, in the ultrasound image U displayed on the display device 8, the blood vessel B is highlighted in the first form, and for example, is highlighted to be filled with the highlight color.

After the execution of Step S3, the process progresses to Step S9 described below.

On the other hand, in a case where the operator inserts the insert C into the subject at the time of the execution of Step S2, both the blood vessel B and the insert C are detected in the ultrasound image U. In this case, Step S4 is executed, and in Step S4, the image analysis unit 9 measures and specifies the distance D between the blood vessel B and the insert C as the relative positional relationship between the detected blood vessel B and insert C. In subsequent Step S5, the apparatus controller 13 determines whether or not the distance D specified in Step S4 is smaller than the threshold value.

In a case where determination is made in Step S5 that the distance D is greater than the threshold value, Step S3 described above is executed, and the apparatus controller 13 performs control such that the highlighting unit 10 highlights the blood vessel B in the ultrasound image U in the first form. After the execution of Step S3, the process progresses to Step S9 described below.

On the other hand, in a case where determination is made that the distance D is smaller than the threshold value, subsequent Step S6 is executed, and in Step S6, the apparatus controller 13 determines whether or not the distance D specified in Step S4 is smaller than the threshold value for enlarged display.

In a case where the distance D is equal to the threshold value, any of Step S3 or Step S6 may be executed.

In a case where determination is made in Step S6 that the distance D is greater than the threshold value for enlarged display, Step S7 is executed, and in Step S7, the apparatus controller 13 performs control such that the highlighting unit 10 highlights the blood vessel B in the ultrasound image U in the second form, and in more detail, highlights the blood vessel B in the designation mark display form. In the ultrasound image U displayed on the display device 8, the instruction mark M consisting of the dotted line-shaped frame line surrounding the blood vessel B is displayed near the blood vessel B and the blood vessel B is highlighted.

In Step S7, the apparatus controller 13 performs control such that the highlighting unit 10 displays the instruction mark M around the blood vessel B in a state in which the interval t depending on the threshold value for enlarged display is provided between the blood vessel B and the instruction mark M (see FIG. 8). With this, it is possible to visualize and display the threshold value for enlarged display as the instruction mark M in the ultrasound image U.

In regard to the display size of the instruction mark M, the set contents can be changed through the input device 14 or can be changed for each operator corresponding to the identification information of the operator.

After the execution of Step S7, the process progresses to Step S9.

On the other hand, in a case where determination is made in Step S6 that the distance D is smaller than the threshold value for enlarged display, Step S8 is executed, and in Step S8, the apparatus controller 13 performs control such that the highlighting unit 10 highlights the blood vessel B in the ultrasound image U in the second form, and in more detail, highlights the blood vessel B in the enlarged display form. With this, the enlarged display image KU including the blood vessel B is displayed on the display device 8, and in the enlarged display image KU, the blood vessel B is enlarged and displayed compared to the ultrasound image U as an original image. In this case, to improve the insertion accuracy of the insert C, it is preferable that the distal end of the insert C is enlarged and displayed in the enlarged display image KU along with the blood vessel B (see FIG. 9).

In regard to the display range in the ultrasound image U enlarged displayed in the enlarged display image KU and the display size of the enlarged display image KU, the set contents can be changed through the input device 14 or can be changed for each operator corresponding to the identification information of the operator.

After the execution of Step S7, the process progresses to Step S9.

In Step S9, determination is made whether or not to end the operation of the ultrasound diagnostic apparatus 1. For example, in a case where the operator inputs an instruction for the guidance on ending the operation of the ultrasound diagnostic apparatus 1 through the input device 14 or the like, determination is made to end the operation of the ultrasound diagnostic apparatus 1, and in a case where the instruction to end the operation of the ultrasound diagnostic apparatus 1 is not input, determination is made not to end the operation of the ultrasound diagnostic apparatus 1. In a case where determination is made not to end the operation of the ultrasound diagnostic apparatus 1, the process returns to Step S1, the ultrasound image U is newly generated, and then, the steps after Step S2 are repeated.

On the other hand, in a case where determination is made to end the operation of the ultrasound diagnostic apparatus 1, the operation of the ultrasound diagnostic apparatus 1 ends.

As described above, with the ultrasound diagnostic apparatus 1 according to the first embodiment, the blood vessel B and the insert C in the ultrasound image U are detected, and the form in highlighting the blood vessel B is switched based on the relative positional relationship between the detected blood vessel B and the insert C. With this, the blood vessel B of the ultrasound image U is highlighted in an appropriate form depending on an insertion state of the insert C. Specifically, in an initial stage of an insertion operation of the insert C, the blood vessel B is displayed to be filled with the highlight color, or the like, such that the blood vessel B can be made conspicuous and easily found in the ultrasound image U.

On the other hand, in a case where the blood vessel B is displayed to be filled with the highlight color in a stage where the insertion operation progresses and the distal end of the insert C is brought close to the blood vessel B, the vascular wall of the blood vessel B is hardly viewed instead, and this may be obstructive in a case where the operator puts the distal end of the insert C in the vascular wall. Accordingly, in the stage where the distal end of the insert C is brought close to the blood vessel B, the blood vessel B is highlighted in a form (second form) without interference with the blood vessel B, such as a form in which the instruction mark M is displayed around the blood vessel B or a form in which the blood vessel B is enlarged and displayed. With this, a tomographic image of the vascular wall of the blood vessel B is clearly visible, and the operator can appropriately put the distal end of the insert C in the vascular wall.

Figure 14:
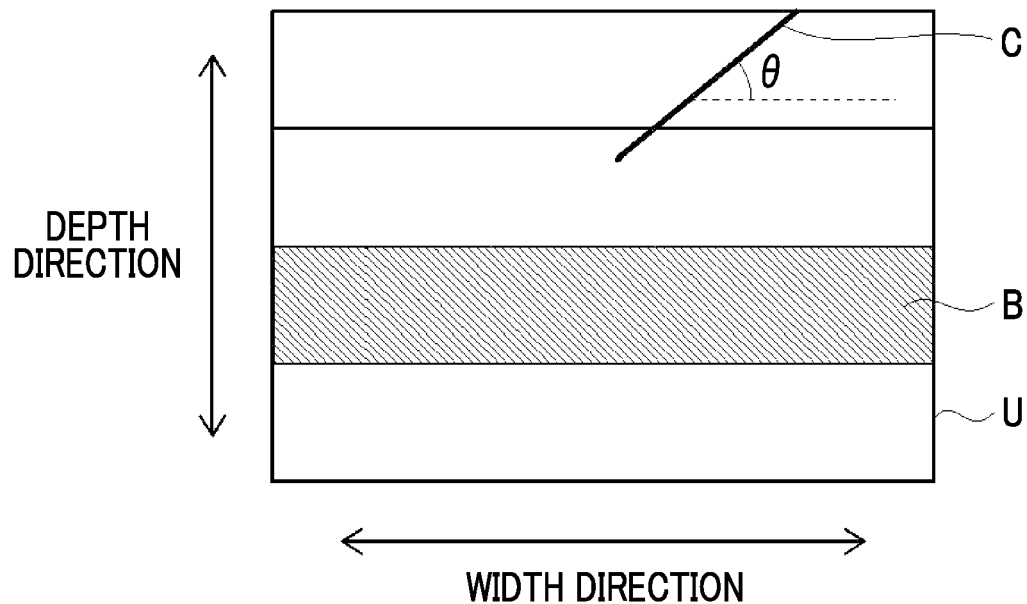
FIG. 14 is a diagram showing an ultrasound image in which a longitudinal section of the blood vessel is highlighted in the first form.
Figure 15:
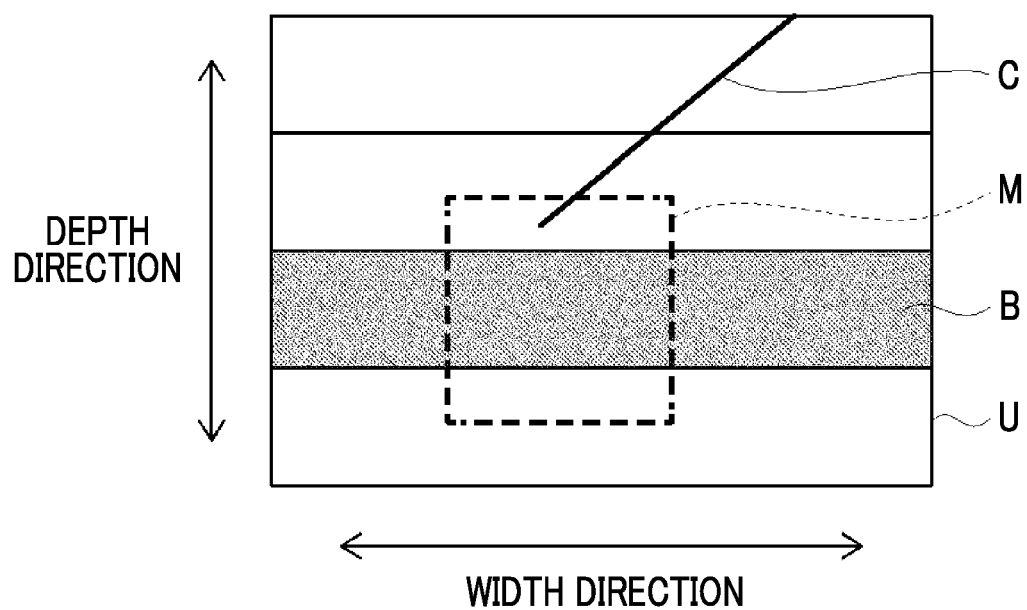
FIG. 15 is a diagram showing an ultrasound image in which the longitudinal section of the blood vessel is highlighted in the second form (first view).
Figure 16:
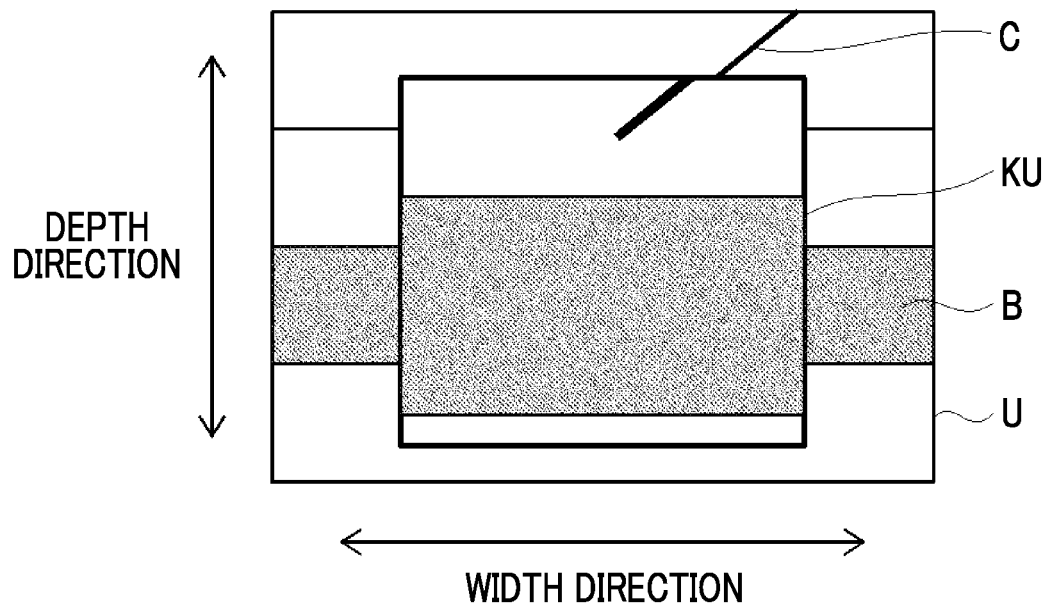
FIG. 16 is a diagram showing the ultrasound image in which the longitudinal section of the blood vessel is highlighted in the second form (second view).
Figure 17:
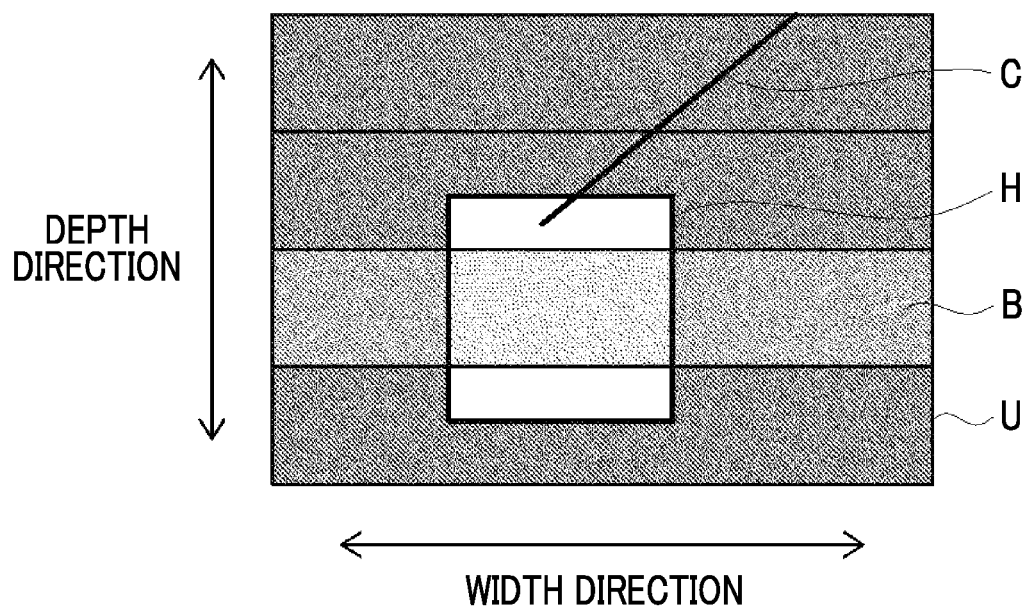
FIG. 17 is a diagram showing the ultrasound image in which the longitudinal section of the blood vessel is highlighted in the second form (third view).

In the above-described case, although the transverse section of the blood vessel that is observed in the minor axis method (crossover method) is highlighted, as shown in FIGS. 14 to 17, a longitudinal section of the blood vessel that is observed in a major axis method (paralleling method) can be highlighted. FIG. 14 shows an ultrasound image U in which a longitudinal section of the blood vessel B is highlighted to be filled with the highlight color. FIG. 15 shows an ultrasound image U in which a portion in the blood vessel B estimated that the insert C enters is highlighted to be surrounded by an instruction mark M consisting of a frame line. FIG. 16 shows an ultrasound image U in which a portion in the blood vessel B estimated that the insert C enters is enlarged and highlighted. FIG. 17 shows an ultrasound image U in which a portion in the blood vessel B estimated that the insert C enters is highlighted with brightness brighter than the vicinity.

In the ultrasound images U shown in FIGS. 14 to 17, a longitudinal section of the insert C is rendered along with the longitudinal section of the blood vessel B. Here, the longitudinal section of the blood vessel B indicates a cut section of the blood vessel B along an extension direction of the blood vessel B, and the longitudinal section of the insert C indicates a cut section of the insert C along the extension direction of the insert C.

In the above-described case, the distance D between the blood vessel B and the insert C is specified as the relative positional relationship between the blood vessel B and the insert C detected by the image analysis unit 9. The present invention is not limited thereto, and a physical quantity other than the distance D may be specified. For example, an insertion angle (in FIG. 14, an angle represented by a symbol 0) of the insert C with respect to the detected blood vessel B may be specified. Here, the insertion angle θ is an angle between the extension directions of the blood vessel B and the insert C that are observed in the major axis method (paralleling method).

As a positional relationship other than the above-described physical quantity, a circular range at a predetermined distance from the contour of the detected blood vessel B may be set in the ultrasound image U, and a positional relationship between the range and the insert C (specifically, whether or not the distal end of the insert C is within the above-described range) may be specified. In this case, the highlighting form of the blood vessel B may be changed based on the specified positional relationship.

In the above-described case, the transmission circuit 3 and the reception circuit 4 are provided in the ultrasound probe 21, and the image generation unit 6 is provided in the processor 22. The present invention is not limited thereto, and the transmission circuit 3, the reception circuit 4, and the image generation unit 6 may be provided in the ultrasound probe 21. In this case, a form is made in which the ultrasound image (B mode image signal) is generated by the ultrasound probe 21, and the processor 22 receives the ultrasound image sent from the ultrasound probe 21.

The transmission circuit 3 may be provided in the ultrasound probe 21, and the reception circuit 4 and the image generation unit 6 may be provided in the processor 22. Alternatively, the transmission circuit 3, the reception circuit 4, and the transmission and reception circuit 5 may be provided on the processor 22 side. In this case, a form is made in which the electric signal (analog signal) output from each of a plurality of transducers of the transducer array 2 that receives the ultrasound echo is transmitted from the ultrasound probe 21 to the processor 22, and the AD conversion of the electric signal, the generation of the sound ray signal, and the generation of the ultrasound image (B mode image signal) are performed on the processor 22 side.

In the above-described case, the highlighting form of the blood vessel B is changed in three stages, and specifically, as the insert C is brought close to the blood vessel B, the highlighting form changes in an order of the filling form with the highlight color, the instruction mark display form, and the enlarged display form. The present invention is not limited thereto, and the number of times of switching of the highlighting form of the blood vessel B may be two times or may be four times or more.

In the above-described case, in the ultrasound image U in which the blood vessel B is highlighted, the threshold value for enlarged display is visualized and displayed as the instruction mark M (frame line) along with the blood vessel B (see FIG. 8). In this case, though not particularly shown, the above-described threshold value may be visualized and displayed as the instruction mark M (frame line) along with the blood vessel B in the same manner.

In the above-described case, although a case where the blood vessel is displayed in the instruction mark display form, and then, displays in the enlarged display form has been described as an example where the blood vessel B highlighted in the second form, a case where the blood vessel B is displayed in the spotlight display form is also considered. In this case, for example, as shown in FIG. 10, it is desirable that both the distal end of the insert C and the blood vessel B are included in the spotlight display region H. With this, the operator can perform the insertion operation of the insert C while recognizing a tissue between the blood vessel B and the insert C. In a stage where the distance D between the insert C and the blood vessel B is smaller than a predetermined value (for example, a value corresponding to the threshold value for enlarged display), highlighting in the spotlight display form may be stopped. In this manner, it is possible to easily find the vascular wall of the blood vessel B immediately before the distal end of the insert C is put in the blood vessel B.

Figure 18A:
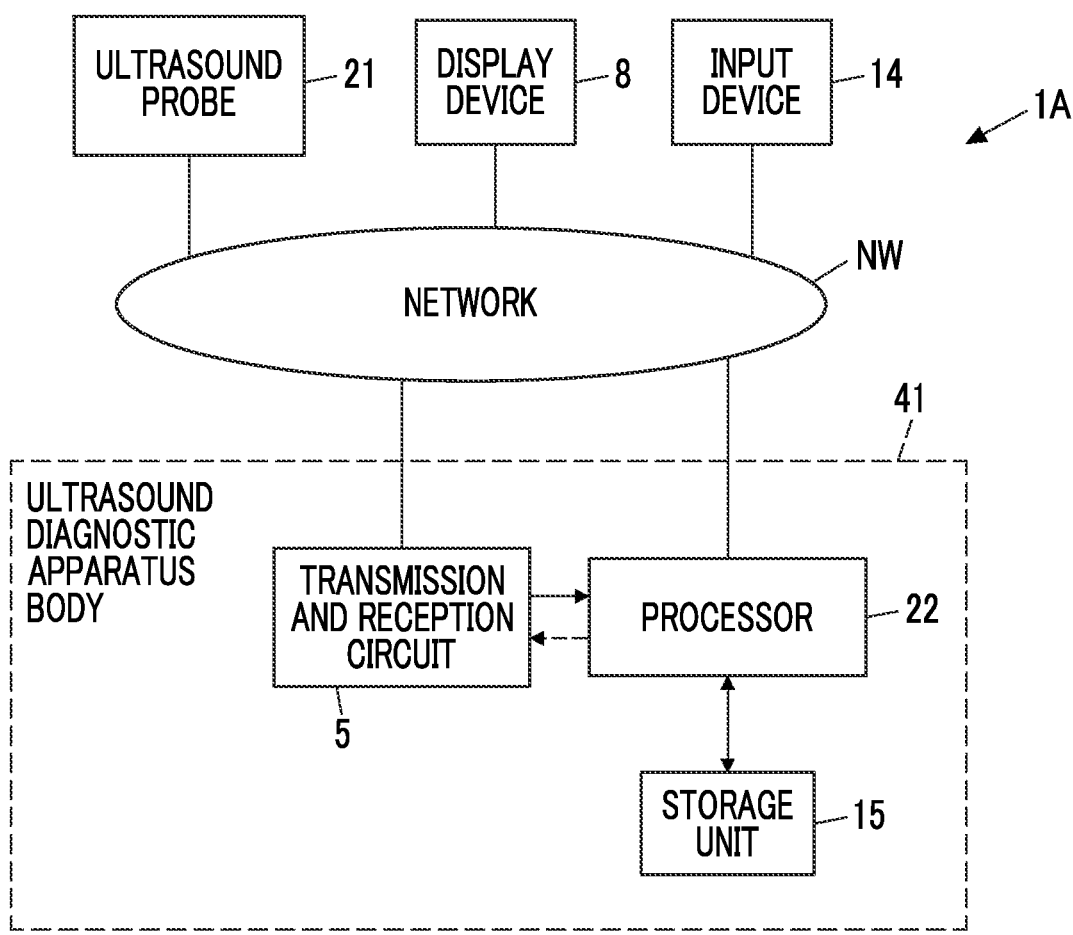
FIG. 18A is a diagram showing the configuration of an ultrasound diagnostic apparatus in which an ultrasound probe, a processor, a display device, and an input device are connected through a network.
Figure 18B:
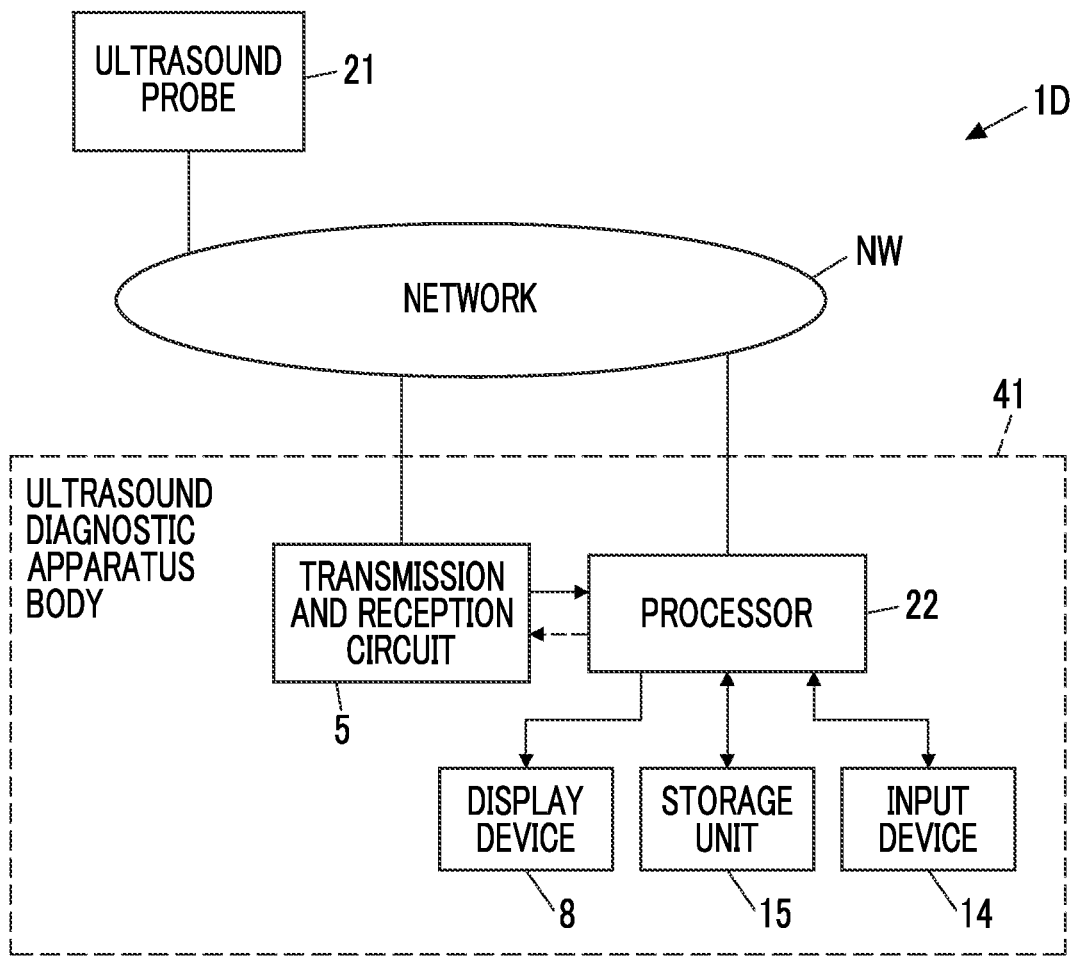
FIG. 18B is a diagram showing a configuration in which the ultrasound probe is connected to an ultrasound diagnostic apparatus body through the network.

In the above-described case, although a configuration in which the display device 8, the input device 14, and the ultrasound probe 21 are connected directly to the processor 22 has been described, for example, as shown in FIGS. 18A and 18B, a configuration may be made in which the display device 8, the input device 14, the ultrasound probe 21, and the processor 22 are connected indirectly through a network NW. In this case, the connection of each piece of equipment described above and the network NW may be wired connection or may be wireless connection.

In an ultrasound diagnostic apparatus 1A of the configuration shown in FIG. 18A, the display device 8, the input device 14, and the ultrasound probe 21 are connected to an ultrasound diagnostic apparatus body 41 through the network NW. The ultrasound diagnostic apparatus body 41 is not provided with the display device 8, the input device 14, and the ultrasound probe 21, and is configured with the transmission and reception circuit 5, the storage unit 15, and the processor 22, compared to the ultrasound diagnostic apparatus 1 of the configuration shown in FIG. 1.

In the ultrasound diagnostic apparatus 1A of the configuration shown in FIG. 18A, the above-described ultrasound diagnostic apparatus body 41 may be used as a remote server. In this case, for example, since the operator can diagnose the subject by preparing only the display device 8, the input device 14, and the ultrasound probe 21 at the hand of the operator, it is possible to improve convenience in ultrasound diagnosis.

In the ultrasound diagnostic apparatus 1A of the configuration shown in FIG. 18A, a smartphone or a tablet terminal may be used as the display device 8 and the input device 14. In this case, since the operator can more easily perform ultrasound diagnosis on the subject, it is possible to further improve convenience of ultrasound diagnosis.

In an ultrasound diagnostic apparatus 1D of the configuration shown in FIG. 18B, the display device 8 and the input device 14 are mounted in the ultrasound diagnostic apparatus body 41, and the ultrasound probe 21 is connected to the ultrasound diagnostic apparatus body 41 through the network NW. In this case, the ultrasound diagnostic apparatus body 41 may be configured with a remote server or can be configured with a smartphone or a tablet terminal.

In the above-described case, the blood vessel B detected in the ultrasound image U is highlighted, and the form of highlighting is changed based on the distance D between the blood vessel B and the insert C. In the same manner, the insert C detected in the ultrasound image U may be highlighted, and the form of highlighting may be changed based on the above-described distance D. In this case, for example, the insert C can be displayed to be filled with the highlight color or the instruction mark M consisting of the frame line can be displayed near the distal end of the insert C. When the distal end of the insert C reaches near the blood vessel B, in a case where the insert C is highlighted in the above-described form, there is a possibility that the tomographic image (B mode image) of the vascular wall is hidden. For this reason, in a case where the distal end of the insert C is highlighted near the blood vessel B, it is preferable that the distal end of the insert C is highlighted in a form of being conspicuous while minimizing an area of highlighting, such as providing a point with high brightness and high saturation in the insert C.

Second Embodiment

Figure 19:
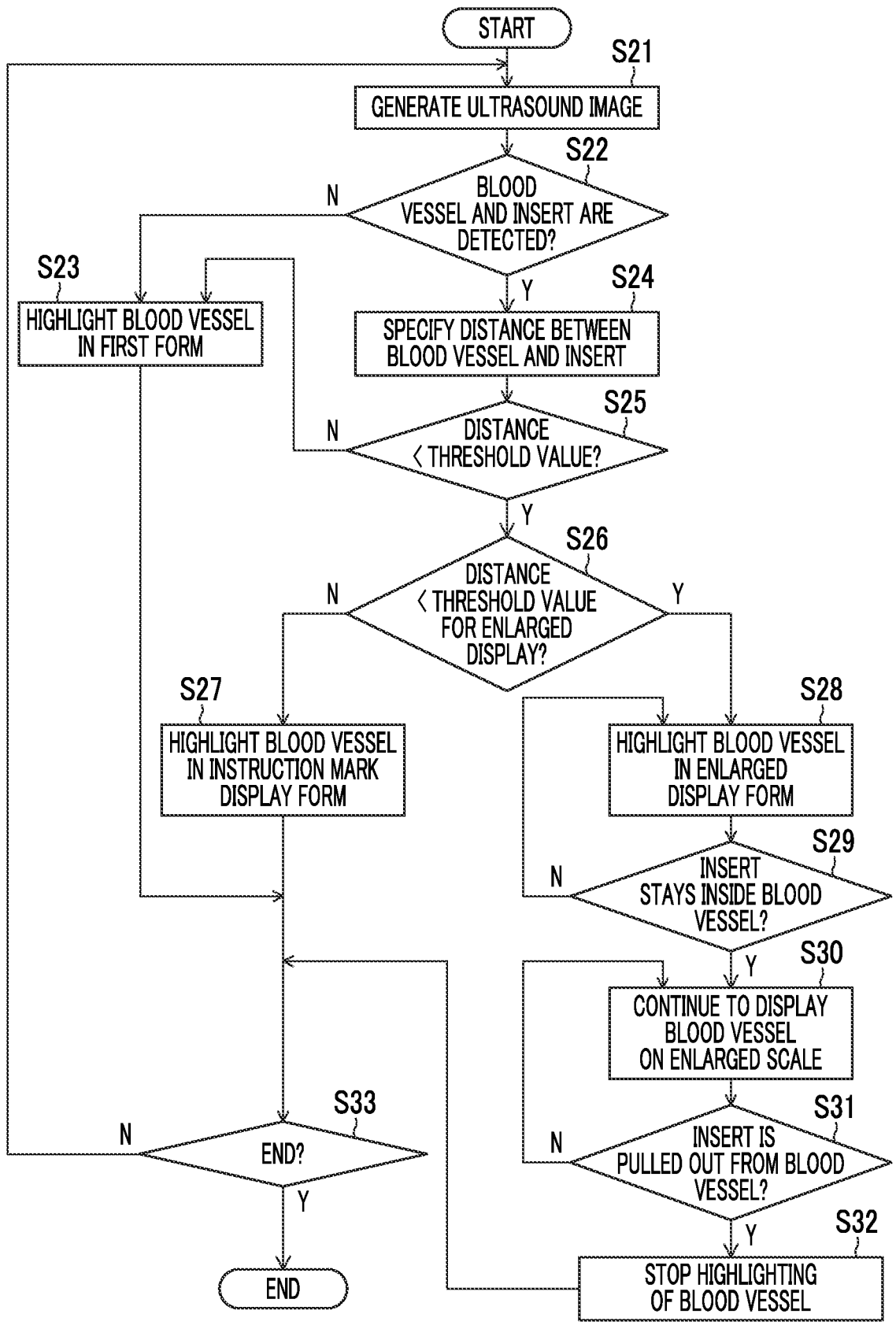
FIG. 19 is a flowchart illustrating the operation of an ultrasound diagnostic apparatus according to a second embodiment of the present invention.

In the echo guided puncture method, although the operator confirms the ultrasound image to recognize the position of each of the insert and the blood vessel in a period from when the insert punctures the body surface of the subject until the insert is inserted into the blood vessel inside the subject, the operator may confirm the ultrasound image even after the insert is inserted into the blood vessel. For example, in a case where the insert is a catheter with a puncture needle, after the puncture needle and the catheter break through the vascular wall and enters the vascular wall, the operator removes only the puncture needle as an inner needle, and places a distal end part of the catheter inside the blood vessel. Thereafter, to recognize a state of the catheter placed inside the blood vessel, the operator confirms the ultrasound image in a short period after the catheter is inserted into the blood vessel. In this case, the enlarged display of the blood vessel in the ultrasound image can be continued such that the inside of the blood vessel in a state in which the catheter is placed can be more clearly viewed. Such an embodiment is referred to as a second embodiment, and the embodiment will be described referring to a flowchart shown in FIG. 19.

The configuration of an ultrasound diagnostic apparatus according to the second embodiment is substantially the same as the configuration of the ultrasound diagnostic apparatus according to the above-described first embodiment.

In a display flow of an ultrasound image by the ultrasound diagnostic apparatus according to the second embodiment, Steps S21 to S28 are the same as Steps S1 to S8 in the display flow according to the first embodiment.

After the execution of Step S28, Step S29 is executed, and in Step S29, the apparatus controller 13 determines whether or not a part of the insert C is inserted into the blood vessel B and stays inside the blood vessel B. Here, a state in which a part of the insert C stays inside the blood vessel B corresponds to, for example, a state in which after the catheter with a puncture needle breaks through the vascular wall of the blood vessel B, only the puncture needle is removed and the distal end of the catheter is placed inside the blood vessel B.

In a case where the apparatus controller 13 determines that a part of the insert C stays inside the blood vessel B, next Step S30 is executed. On the contrary, in a case where the apparatus controller 13 determines that a part of the insert C is not yet inserted into the blood vessel B and a part of the insert C does not stay inside the blood vessel B, the process returns to Step S28.

In Step S30, the apparatus controller 13 performs control such that the highlighting unit 10 continues to enlarge and display the blood vessel B in the ultrasound image U. After Step S30 is executed, in subsequent Step S31, the apparatus controller 13 determines whether or not a part of the insert C is removed from the blood vessel B.

In a case where the apparatus controller 13 determines that a part of the insert C is not removed from the blood vessel B (that is, stays inside the blood vessel B), the process returns to Step S30. On the other hand, in a case where determination is made that a part of the insert C is removed from the blood vessel B, Step S32 is executed, and in Step S32, the apparatus controller 13 performs control such that the highlighting unit 10 stops the highlighting of the blood vessel B. With this, in the ultrasound image U, the blood vessel B is displayed in a normal form (a form of being not highlighted).

Thereafter, like the case of the first embodiment, Step S33 of determining whether or not to end the operation of the ultrasound diagnostic apparatus is executed, and in a case where determination is made not to end the operation of the ultrasound diagnostic apparatus, the process returns to Step S21. Thereafter, the processing after Step S22 is repeated. On the other hand, in a case where determination is made to end the operation of the ultrasound diagnostic apparatus, the operation of the ultrasound diagnostic apparatus ends.

As above, in the second embodiment, while the insert C is inserted into the blood vessel B and a part of the insert C stays inside the blood vessel B, the blood vessel B continues to be enlarged and displayed, whereby the blood vessel B in a state in which a part of the insert C enters is easily viewed (easily confirmed) for the operator.

In the above-described case, although the blood vessel B continues to be enlarged and displayed while a part of the insert C stays inside the blood vessel B, the present invention is not limited thereto. For example, in a case where determination is made that a part of the insert C stays inside the blood vessel B, the apparatus controller 13 may perform control such that the highlighting unit 10 stops the highlighting of the blood vessel B in the ultrasound image U. In this case, while a part of the insert C stays inside the blood vessel B, the blood vessel B in the ultrasound image U is displayed in the normal form (a form of being not highlighted). With this, the operator can confirm the ultrasound image U in a comparatively wide range including the insert C and the blood vessel B, and for example, can easily find out a tissue, phlebitis, or the like on an insertion path of the insert C.

The ultrasound diagnostic apparatus according to the second embodiment is usable in a case of observing the blood vessel B and the insert C in the minor axis method, and is also usable in a case of confirming the blood vessel B and the insert C in the major axis method.

Third Embodiment

In the first embodiment described above, the highlighting form of the blood vessel B has been changed based on the distance D between the blood vessel B and the insert C. When the insert C is near the blood vessel B, to improve operability (ease of insertion of the insert C) in a case where the operator inserts the insert C into the blood vessel B, the blood vessel B has been displayed in the second form while avoiding interference with the blood vessel B.

Note that, in a case where the insert C is not correctly inserted, the insert C may not arrive at the blood vessel B even though the insert C is positioned near the blood vessel B, and in this case, the blood vessel B is not necessarily highlighted in the second form to improve operability. In view of this, a range in which the insert C is insertable into the blood vessel B is set as an effective operation region in the ultrasound image U, and only in a case where the distal end of the insert C in the ultrasound image U is within the effective operation region, the blood vessel B can be highlighted in the second form. Such an embodiment is referred to as a third embodiment, and the embodiment will be described below in detail.

The configuration of an ultrasound diagnostic apparatus according to the third embodiment is substantially the same as the configuration of the ultrasound diagnostic apparatus according to the above-described first embodiment.

In the third embodiment, in a case where the blood vessel B and the insert C in the ultrasound image U are detected, the image analysis unit 9 estimates an insertion direction of the insert C. In this case, the image analysis unit 9 detects a trajectory of the distal end of the insert C by analyzing ultrasound images U of a plurality of frames continuously generated by the image generation unit 6, and estimates the insertion direction of the insert C based on the detected trajectory of the distal end.

Figure 20:
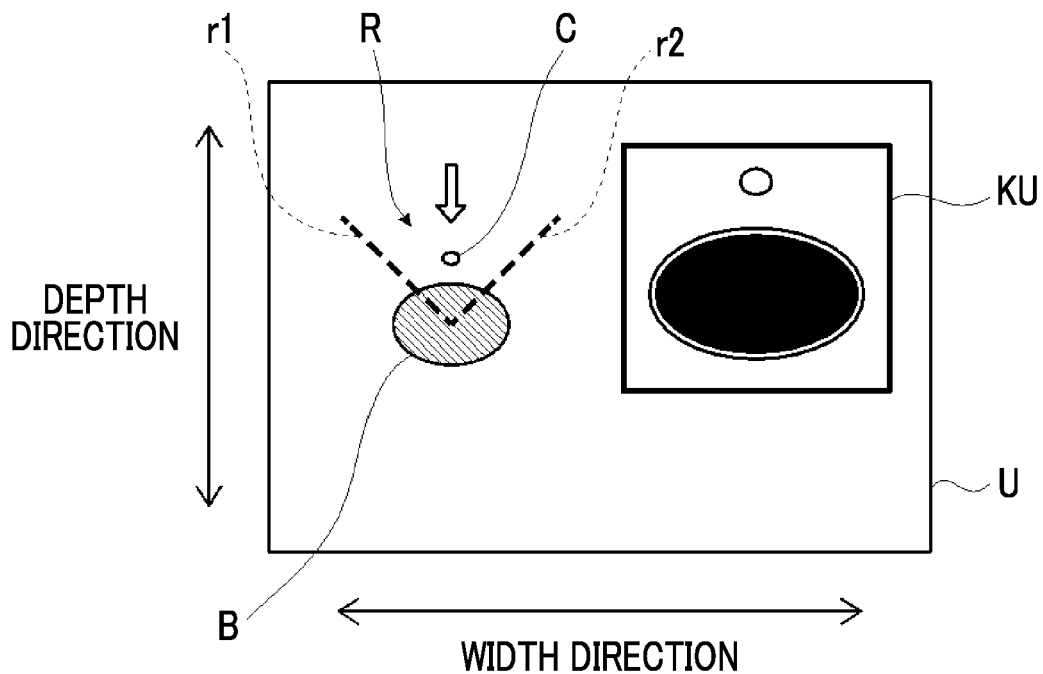
FIG. 20 is a diagram showing an ultrasound image that is displayed by an ultrasound diagnostic apparatus according to a third embodiment of the present invention, and represents a state in which an insert is inside an effective operation region (first view).
Figure 21:
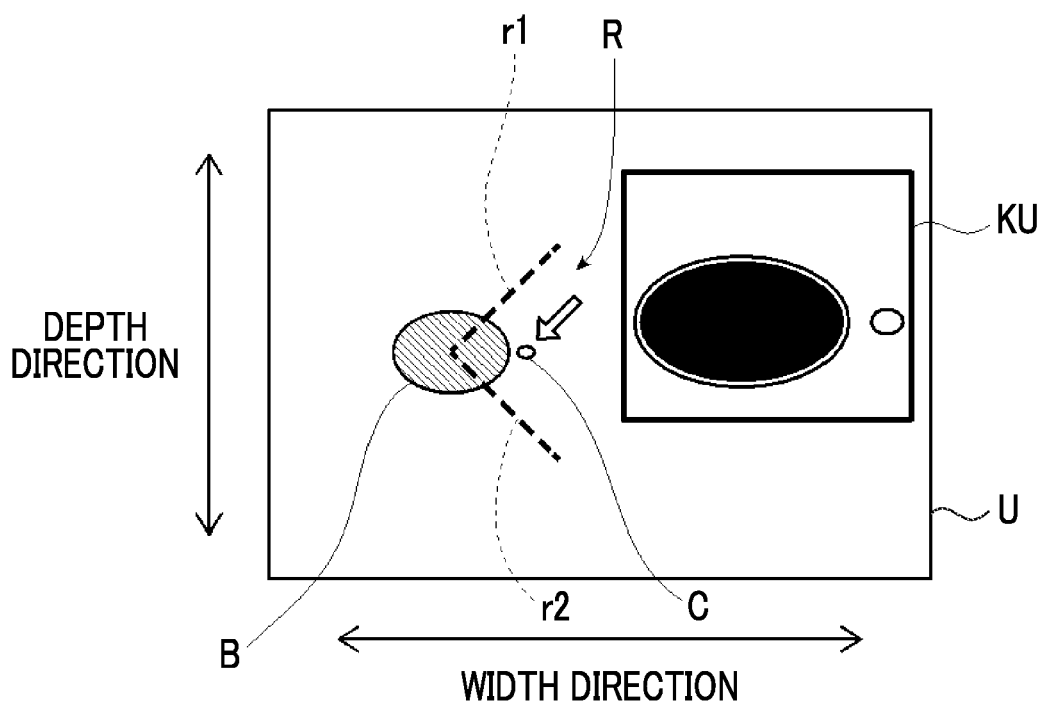
FIG. 21 is a diagram showing the ultrasound image that is displayed by the ultrasound diagnostic apparatus according to the third embodiment of the present invention, and represents a state in which the insert is inside the effective operation region (second view).

In a case where the image analysis unit 9 detects the blood vessel B and the insert C, the apparatus controller 13 sets an effective operation region R in the ultrasound image U based on a position of the blood vessel B detected by the image analysis unit 9 and the insertion direction of the insert C estimated by the image analysis unit 9. As shown in FIGS. 20 and 21, the effective operation region R is a region widened in a fan shape from the center of the blood vessel B, and boundary positions (edges) on both sides are defined by a pair of boundary lines r1 and r2 far from each other at about 120 degrees. An orientation of the effective operation region R (strictly, a direction in which the center line of the effective operation region R extends) is changed depending on the estimated insertion direction (in FIGS. 20 to 23, described with an outlined arrow) of the insert C. For example, in a case where the insertion direction is parallel to or substantially parallel to the depth direction of the ultrasound image U, as shown in FIG. 20, the effective operation region R is set to face upward. In a case where the insertion direction is inclined with respect to the depth direction, as shown in FIG. 21, the effective operation region R is set to face sideways (left or right).

Then, in a case where the distance D between the blood vessel B and the insert C specified by the image analysis unit 9 is smaller than the threshold value, the apparatus controller 13 determines whether or not the distal end of the insert C is within the effective operation region R. In a case where determination is made that the distal end of the insert C is within the effective operation region R, as shown in FIGS. 20 and 21, the apparatus controller 13 performs control such that the highlighting unit 10 highlights the blood vessel B in the second form. In FIGS. 20 and 21, as an example of the second form, an example where the blood vessel B is highlighted in the enlarged display form is shown.

Figure 22:
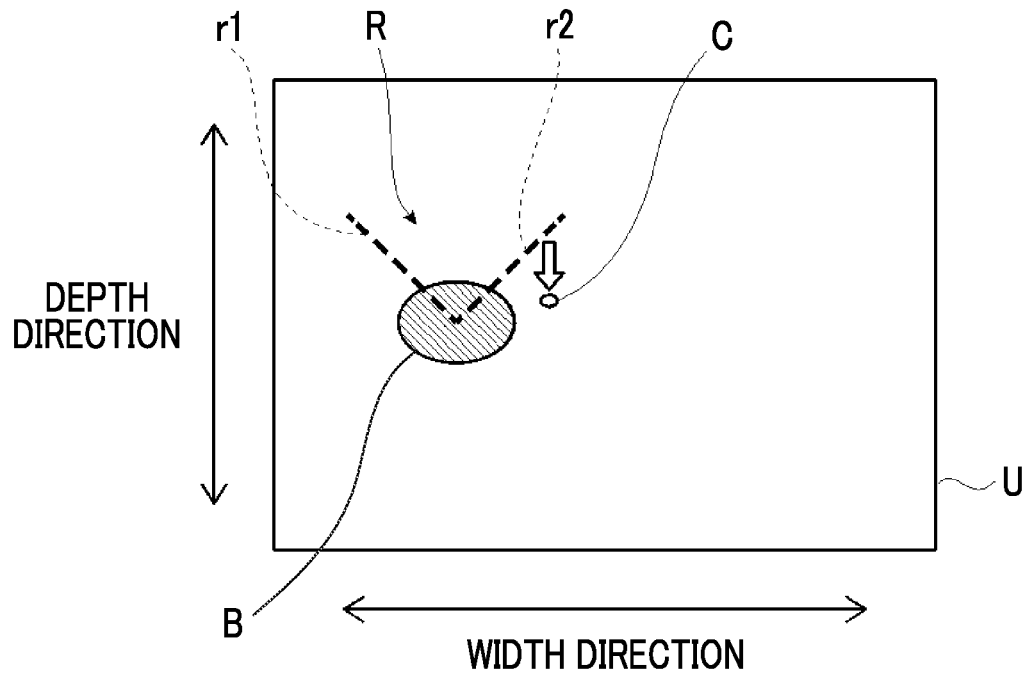
FIG. 22 is a diagram showing an ultrasound image that is displayed by the ultrasound diagnostic apparatus according to the third embodiment of the present invention, and represents a state in which the insert is outside the effective operation region (first view).
Figure 23:
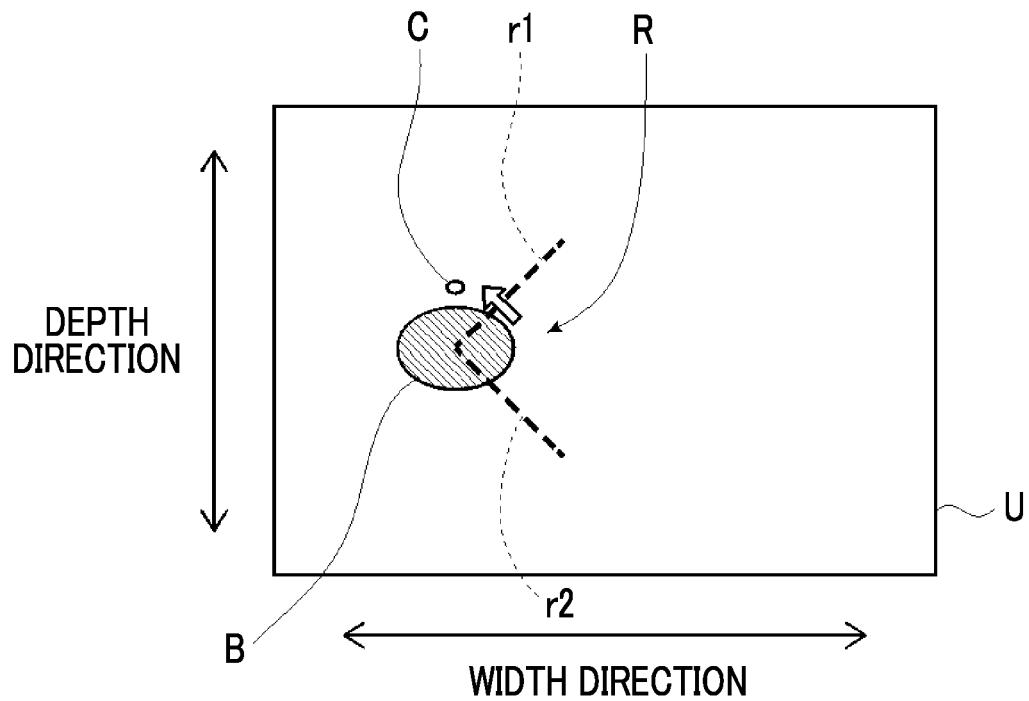
FIG. 23 is a diagram showing the ultrasound image that is displayed by the ultrasound diagnostic apparatus according to a third embodiment of the present invention, and represents a state in which the insert is outside the effective operation region (second view).

On the other hand, in a case where determination is made that the distal end of the insert C is outside the effective operation region R, as shown in FIGS. 22 and 23, the apparatus controller 13 performs control such that the highlighting unit 10 highlights the blood vessel B in the first form. In FIGS. 22 and 23, as an example of the first form, an example where the blood vessel B is highlighted to be filled with the highlight color is shown.

As above, in the third embodiment, only when the distance D between the blood vessel B and the insert C is smaller than the threshold value, and the distal end of the insert C is within the effective operation region R, the highlighting form of the blood vessel B is set to the second form. That is, even though the insert C is positioned near the blood vessel B, in a case where the insert C cannot be inserted into the blood vessel B (for example, in a case where there is no blood vessel B in a running direction of the insert C or in a case where the insert C does not arrive at the blood vessel B even though the running direction of the insert C is slightly changed), the highlighting form of the blood vessel B is maintained in the first form. With this, it is possible to make the operator notice a state in which the insert C is not inserted into the blood vessel B in this situation.

Considering usability for the operator, it is preferable that the highlighting unit 10 highlights the effective operation region R set by the apparatus controller 13 along with the blood vessel B detected by the image analysis unit 9. For example, a pair of boundary lines r1 and r2 may be displayed in the highlight color.

Figure 24:
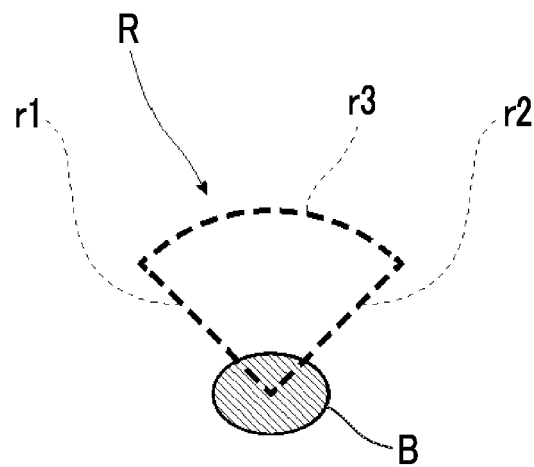
FIG. 24 is a diagram showing a modification example of the effective operation region (first view).

As shown in FIG. 24, the apparatus controller 13 may connect distal ends of a pair of boundary lines r1 and r2 with an arc line r3 and may set a region surrounded by the lines as the effective operation region R. In this case, in a case where the arc line r3 is provided at a position far from a contour line of the blood vessel B by a distance depending on the above-described threshold value, it is possible to set the effective operation region R reflecting the above-described threshold value, and in a case where the arc line r3 is further displayed on the ultrasound image U, it is possible to visualize the above-described threshold value.

Figure 25:
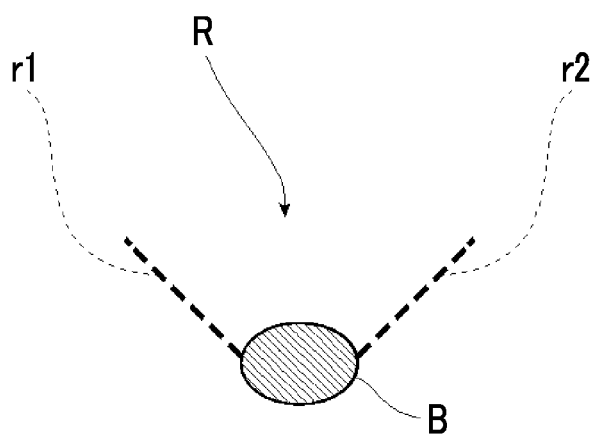
FIG. 25 is a diagram showing the modification example of the effective operation region (second view).

A pair of boundary lines r1 and r2 defining both ends of the effective operation region R may extend from the center of the blood vessel B or may extend from both side ends of the blood vessel B as shown in FIG. 25.

In setting the effective operation region R, the apparatus controller 13 may set the size of the effective operation region R to a given length or may be set to a size decided for each operator. Here, the size of the effective operation region R means the length of the effective operation region R in the width direction of the ultrasound image U (strictly, the shortest distance between the distal end positions of a pair of boundary lines r1 and r2 in the width direction, and referred to as a region width) or an angle (hereinafter, referred to as a region angle) between a pair of boundary lines r1 and r2.

In a case of changing the size of the effective operation region R for each operator, for example, the operator inputs the identification information of the operator and size setting values (specifically, the values of the region width and the region angle) of the effective operation region R through the input device 14. The input setting values are stored in the storage unit 15 in association with the identification information of the operator who inputs the setting values. In this case, in a case where a certain operator inputs the identification information to the input device 14 before the acquisition of the ultrasound image starts, the apparatus controller 13 reads out the size setting values associated with the input identification information among the size setting values stored in the storage unit 15 and sets the effective operation region R having a size indicated by the setting values. The size of the effective operation region R set in this manner is a size corresponding to the identification information of the operator input to the input device 14, and the effective operation region R having the size is appropriately set while reflecting the level of skill or the like of the operator.

The ultrasound diagnostic apparatus according to the third embodiment described above is usable in a case of observing the blood vessel B and the insert C in the minor axis method, and is also usable in a case of confirming the blood vessel B and the insert C in the major axis method.

Fourth Embodiment

Figure 26:
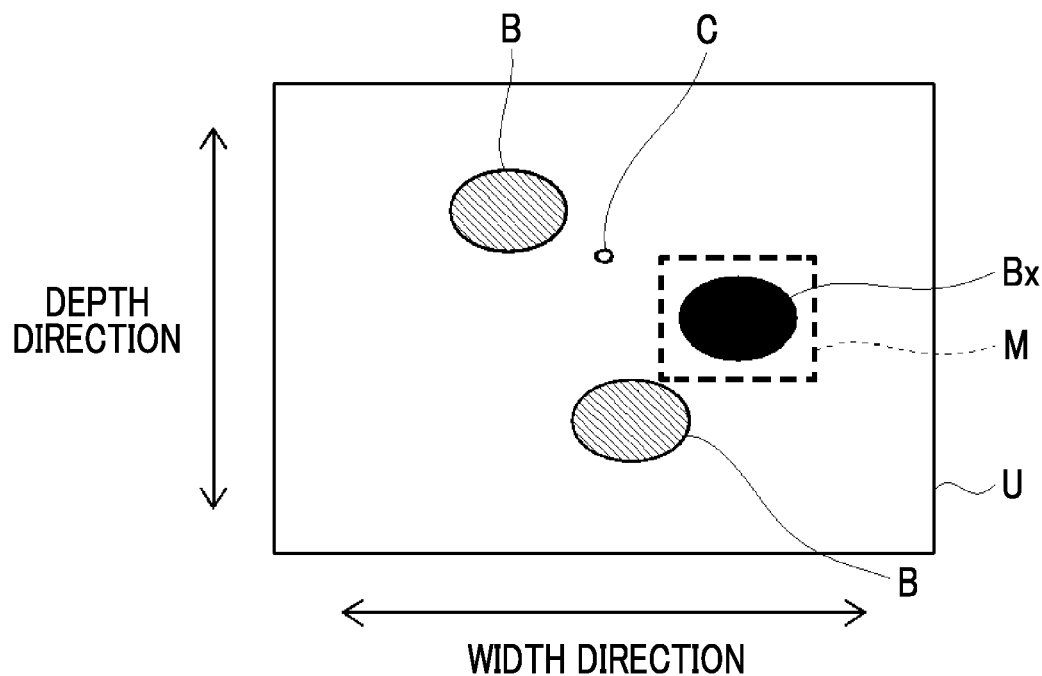
FIG. 26 is a diagram showing an ultrasound image that is displayed by an ultrasound diagnostic apparatus according to a fourth embodiment of the present invention (first view).

As shown in FIG. 26, a plurality of blood vessels B may be displayed in the ultrasound image U. In this case, the insert C is actually inserted into only one blood vessel (hereinafter, referred to as a blood vessel Bx) among a plurality of blood vessels B, and the operator particularly gazes the blood vessel Bx in the ultrasound image U. In light of this, when a plurality of blood vessels B are included in the ultrasound image U, only one blood vessel Bx into which the insert C is inserted can be highlighted in the second form. Such an embodiment is referred to as a fourth embodiment, and the embodiment will be described below in detail.

The configuration of an ultrasound diagnostic apparatus according to the fourth embodiment is substantially the same as the configuration of the ultrasound diagnostic apparatus according to the above-described first embodiment.

In the fourth embodiment, the ultrasound image U that is observed in the minor axis method, that is, the ultrasound image U including the transverse section of the blood vessel B and the transverse section of the insert C is a processing target.

In the fourth embodiment, in a case where a plurality of blood vessels B are detected along with the insert C in the ultrasound image U, the image analysis unit 9 specifies the distance D between the blood vessel B and the insert C on each of a plurality of detected blood vessels B. The image analysis unit 9 estimates the insertion direction of the detected insert C. An estimation procedure of the insertion direction is the same as the procedure described in the third embodiment.

In a case where the image analysis unit 9 detects a plurality of blood vessels B, the apparatus controller 13 determines whether or not each of a plurality of blood vessels B detected by the image analysis unit 9 is at a position reachable by the insert C. In this case, the apparatus controller 13 performs the above-described determination based on the insertion direction estimated by the image analysis unit 9. Specifically, the apparatus controller 13 determines the blood vessel B positioned in the insertion direction as viewed from the distal end of the insert C in the ultrasound image U as a blood vessel at a position reachable by the insert C.

Then, the apparatus controller 13 specifies the blood vessel Bx that has the distance D specified by the image analysis unit 9 smaller than the threshold value and is closest to the distal end of the insert C, among the blood vessels B determined at a position reachable by the insert C, and performs control such that the highlighting unit 10 highlights only the blood vessel Bx in the second form. With this, as shown in FIG. 26, only one blood vessel Bx specified by the apparatus controller 13 among a plurality of blood vessels B in the ultrasound image U is highlighted in the second form, and the remaining blood vessels B are highlighted in the first form. In this manner, the operator can easily find out and gaze the blood vessel Bx into which the insert C is actually inserted, when a plurality of blood vessels B are displayed in the ultrasound image U.

In a case shown in FIG. 26, although one blood vessel Bx specified by the apparatus controller 13 is highlighted in the instruction mark display form, highlighting may be performed in other second forms (for example, the enlarged display form).

Figure 27:
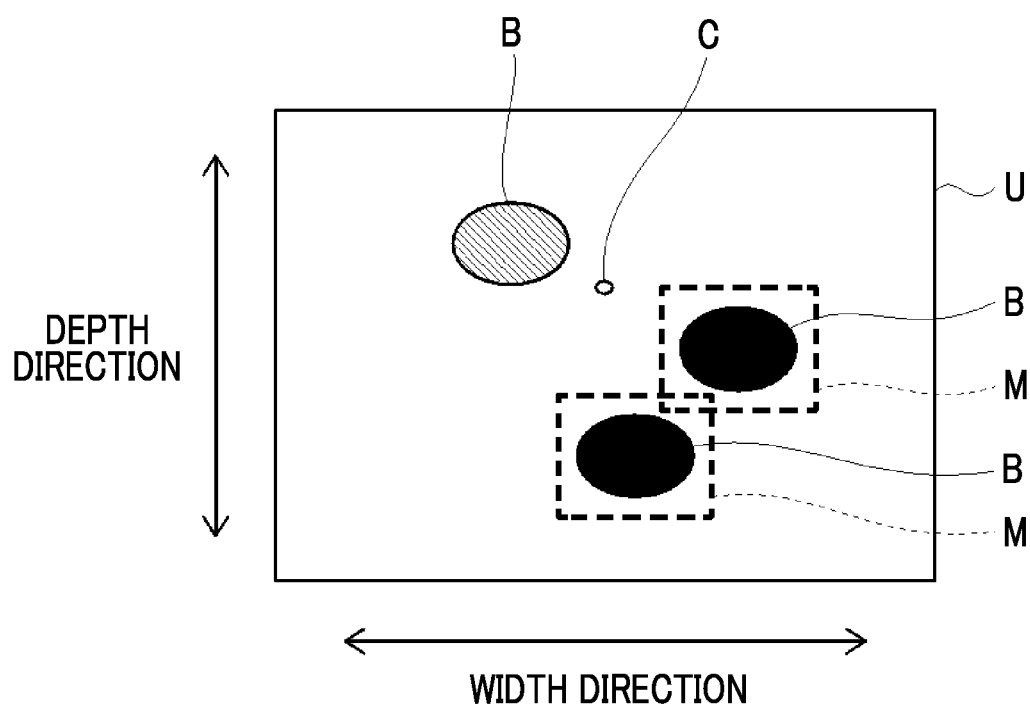
FIG. 27 is a diagram showing the ultrasound image that is displayed by the ultrasound diagnostic apparatus according to the fourth embodiment of the present invention (second view).

As shown in FIG. 27, all the blood vessels B that have the distance D specified by the image analysis unit 9 smaller than the threshold value, among the blood vessels B at a position reachable by the insert C may be highlighted in the second form.

Figure 28:
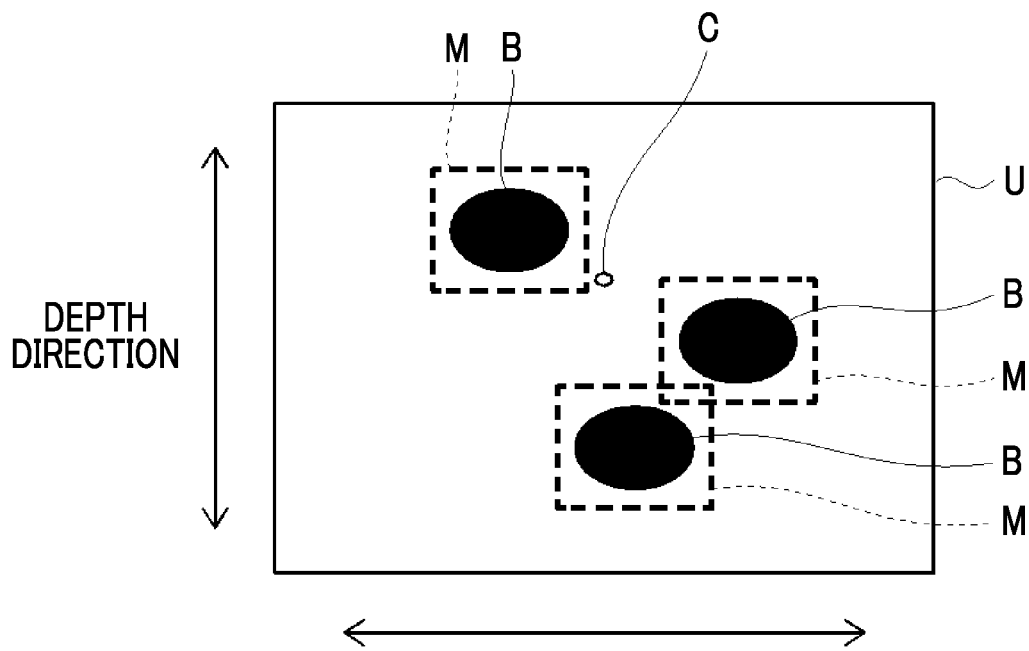
FIG. 28 is a diagram showing the ultrasound image that is displayed by the ultrasound diagnostic apparatus according to the fourth embodiment of the present invention (third view).

As shown in FIG. 28, all the blood vessels B that have the distance D specified by the image analysis unit 9 smaller than the threshold value may be highlighted in the second form regardless of whether or not the blood vessel B is at a position reachable by the insert C.

Figure 29:
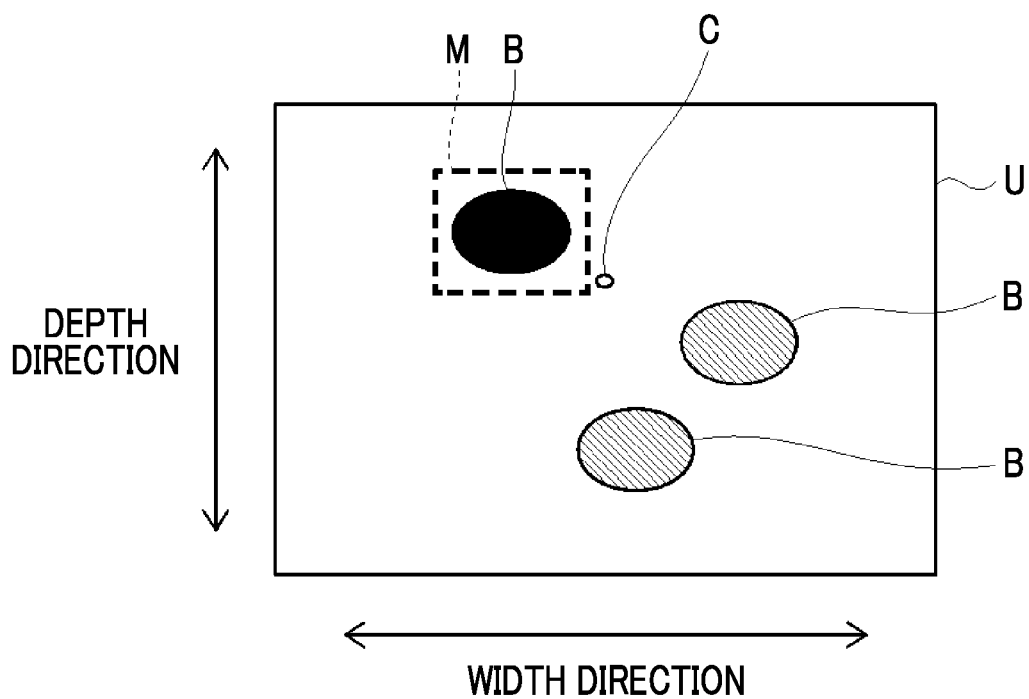
FIG. 29 is a diagram showing the ultrasound image that is displayed by the ultrasound diagnostic apparatus according to the fourth embodiment of the present invention (fourth view).

As shown in FIG. 29, only one blood vessel B that is closest to the distal end of the insert C may be highlighted in the second form regardless of whether or not the blood vessel B is at a position reachable by the insert C.

In the above-described case, in determining whether or not each of a plurality of blood vessels B is at a position reachable by the insert C, the insertion direction of the insert C has been estimated, and the determination is performed based on the estimated insertion direction. The present invention is not limited thereto, and the above-described determination may be performed based on a positional relationship between the blood vessel B and the insert C. For example, determination may be made that the blood vessel B positioned above the distal end of the insert C and the blood vessel B adjacent to the insert C just beside the distal end of the insert C is a blood vessel not at a position reachable by the insert C.

Fifth Embodiment

In the first embodiment described above, the display range or the display size (hereinafter, referred to as "display range or the like") at the time of enlarging and displaying the blood vessel B has been variable, and the display range or the like have been changed depending on the setting information input from the operator through the input device 14. The configuration is developed, and a correspondence relationship between the display range or the like employed when the operator performs the insertion operation of the insert C and a measurement result regarding the insertion operation is learned and specified, whereby it is possible to automatically set the display range or the like depending on the ability and the level of skill of the operator. Such an embodiment is referred to as a fifth embodiment, and the embodiment will be described in detail referring to FIG. 30.

Figure 30:
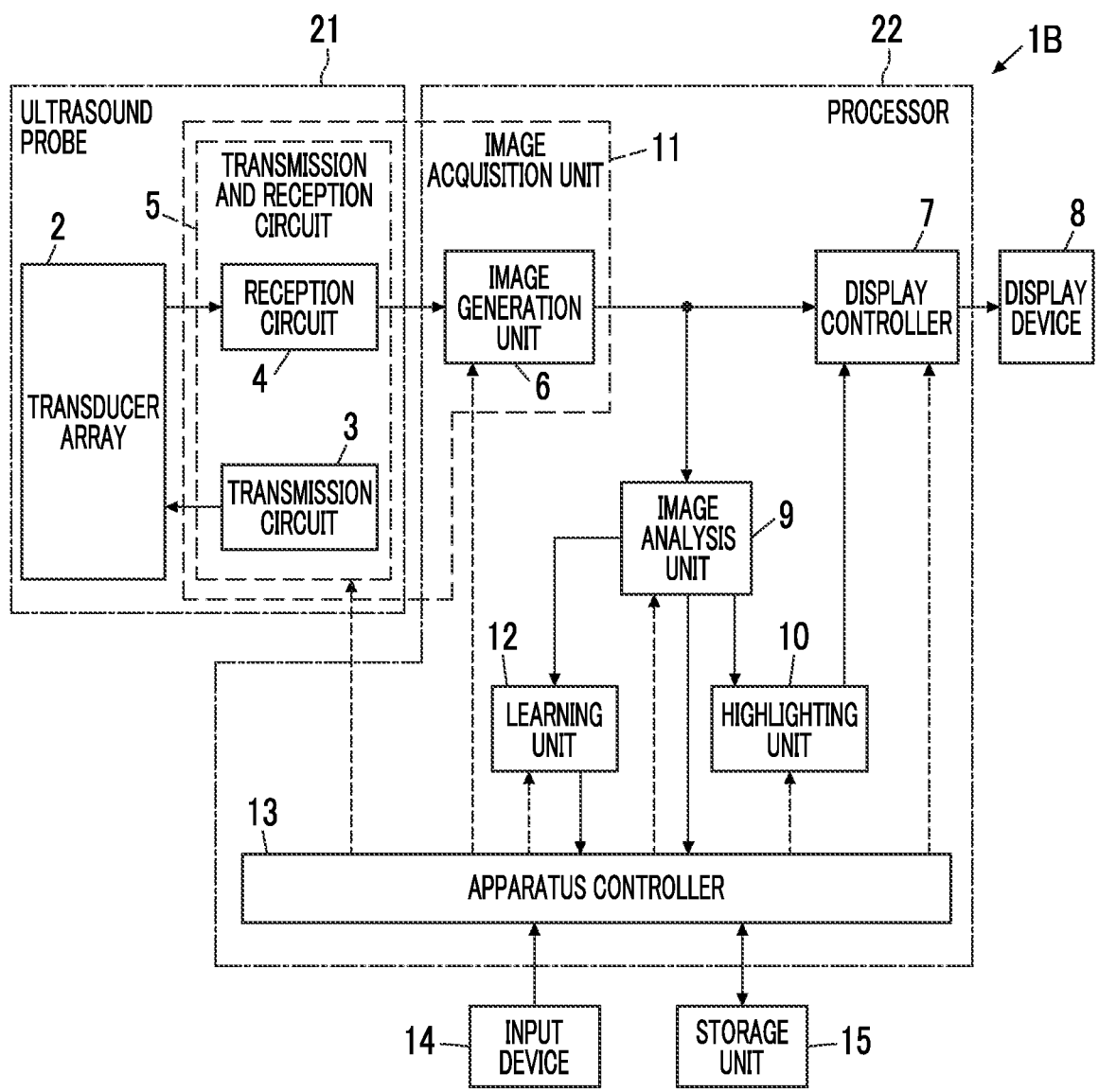
FIG. 30 is a block diagram showing the configuration of an ultrasound diagnostic apparatus according to a fifth embodiment of the present invention.

In an ultrasound diagnostic apparatus 1B according to the fifth embodiment, as shown in FIG. 30, a learning unit 12 is added to the processor 22. In the processor 22, the learning unit 12 is connected to the image analysis unit 9, and the apparatus controller 13 is connected to the learning unit 12.

The learning unit 12 learns a correspondence relationship between the display range or the display size in a case where the highlighting unit 10 highlights the blood vessel B in the second form and a measurement result of measurement processing regarding the insertion operation of the insert. The display range or the display size is set for each operator by the operator inputting the setting information through the input device 14. The measurement processing is executed for each operator by the image analysis unit 9 in a case where the image analysis unit 9 detects the insert C in the ultrasound image U. In the measurement processing, the image analysis unit 9 analyzes the ultrasound images U of a plurality of frames continuously generated by the image generation unit 6, and measures items regarding the insertion operation of the insert C. Specifically, the image analysis unit 9 measures, for example, a range in which the distal end of the insert C is moved within a given time, a movement speed divided from the movement range, or an angle at which the insert C is inserted into the subject.

The learning unit 12 collects the display range or the display size employed by a certain operator and the measurement result of the measurement processing regarding the insertion operation of the insert C by the certain operator as learning data for each operator and executes machine learning using the learning data collected for each operator. In this case, as an algorithm of machine learning, a known algorithm can be used. For example, association rule learning, neural network, deep learning, genetic programming, functional logic programming, random forest, support vector machines, clustering, principal component analysis, cluster analysis, Bayesian networks, and extreme learning machines are usable. In addition, machine learning algorithms that can be developed in the future are also usable.

In the fifth embodiment, in a case where a certain operator inserts the insert C into the subject, the measurement processing by the image analysis unit 9 is executed. Then, the apparatus controller 13 performs control such that the highlighting unit 10 changes the display range or the display size at the time of enlarging and displaying the blood vessel B, depending on the measurement result of the measurement processing. In more detail, the apparatus controller 13 derives the display range or the like corresponding to the measurement result of the measurement processing based on the correspondence relationship learning by the learning unit 12 and performs control such that the highlighting unit 10 enlarges and displays the blood vessel B with the derived display range or the like.

As above, in the fifth embodiment, the correspondence relationship between the display range or the like in enlarging and displaying the blood vessel B and the measurement result of the measurement processing regarding the insertion operation of the insert C is learned, and the display range or the like depending on the measurement result is set based on the correspondence relationship. With this, since an appropriate display range or the like is automatically decided depending on the ability, the level of skill, and the like of the operator on the processor 22 side, usability for the operator is improved. For example, since the operator who is deficient in the level of skill needs to more widely observe the vicinity of the blood vessel B into which the insert C is inserted, a wider display range can be set for such an operator.

In the above-described case, although the display range or the display size at the time of enlarging and displaying the blood vessel B is set depending on the measurement result of the measurement processing regarding the insertion operation of the insert C, the present invention is not limited thereto. The display size of the instruction mark M in highlighting the blood vessel B in the instruction mark display form or the display range or the like of the spotlight display region H in highlighting the blood vessel B in the spotlight display form may be set depending on the measurement result of the measurement processing.

Sixth Embodiment

In the fifth embodiment described above, the display range or the display size (display range or the like) at the time of enlarging and displaying the blood vessel B has been automatically set depending on the ability and the level of skill of the operator. As a modification example, the display range or the like can be automatically set depending on information regarding the operator, for example, information regarding the use of the ultrasound diagnostic apparatus. Such an embodiment is referred to as a sixth embodiment, and the embodiment will be described in detail referring to FIG. 31.

Figure 31:
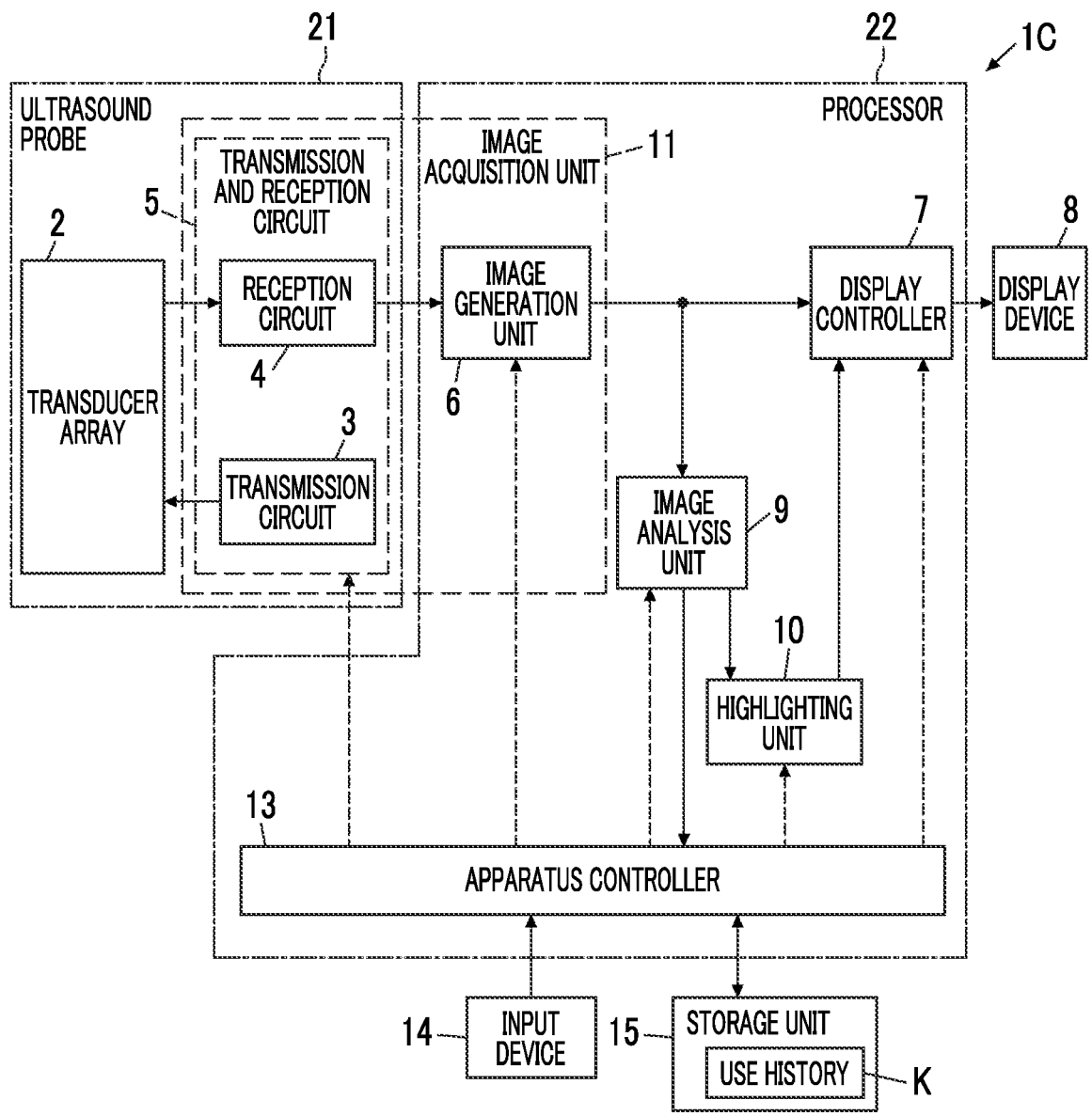
FIG. 31 is a block diagram showing the configuration of an ultrasound diagnostic apparatus according to a sixth embodiment of the present invention.

The configuration of an ultrasound diagnostic apparatus 1C according to the sixth embodiment is substantially the same as the configuration of the ultrasound diagnostic apparatus according to the above-described first embodiment. In contrast, as shown in FIG. 31, the storage unit 15 stores a use history K of each operator, and the embodiment is different from the first embodiment in such a point. The use history K is an example of information regarding the operator, and as the use history of the ultrasound diagnostic apparatus 1C by the operator, specifically, a use count or a use frequency is represented. The storage unit 15 stores the use history K of each operator in association with the identification information of the operator.

In the sixth embodiment, in starting ultrasound image acquisition by the ultrasound diagnostic apparatus 1C, the operator inputs the identification information of the operator through the input device 14. Thereafter, in a case where the blood vessel B in the ultrasound image U is highlighted in the second form, the apparatus controller 13 performs control such that the highlighting unit 10 changes the display range or the like depending on information regarding the operator identified by the identification information input to the input device 14. In detail, the apparatus controller 13 reads out the use history K corresponding to the input identification information from the storage unit 15 and performs control such that the highlighting unit 10 changes the display range or the like depending on the read-out use history K. In this case, for example, as the operator has a large use count of the ultrasound diagnostic apparatus 1C, the apparatus controller 13 can perform control such that the highlighting unit 10 gradually narrows the display range or the like.

As above, in the sixth embodiment, the display range or the like in enlarging and displaying the blood vessel B can be automatically set depending on information regarding the operator, and specifically, the use history K of the ultrasound diagnostic apparatus 1C by the operator. With this, as in the fifth embodiment, since an appropriate display range or the like is automatically decided depending on the experience or the like of the operator on the processor 22 side, usability for the operator is improved.

In the above-described case, although information regarding the operator has been the use history K of the ultrasound diagnostic apparatus 1C by the operator, the present invention is not limited thereto. For example, a configuration may be made in which the display range or the like is automatically set depending on a profile (in particular, contents related to the use of the ultrasound diagnostic apparatus) of the operator.

EXPLANATION OF REFERENCES

1, 1A, 1B, 1C, 1D: ultrasound diagnostic apparatus
2: transducer array
3: transmission circuit
4: reception circuit
5: transmission and reception circuit
6: image generation unit
7: display controller
8: display device
9: image analysis unit
10: highlighting unit
11: image acquisition unit
12: learning unit
13: apparatus controller
14: input device
15: storage unit
21: ultrasound probe
22: processor
23: amplification unit
24: AD conversion unit
25: beam former
26: signal processing unit
27: DSC
28: image processing unit
41: ultrasound diagnostic apparatus body
B, Bx: blood vessel
C: insert
D: distance
H: spotlight display region
K: use history
KU: enlarged display image
M: instruction mark
NW: network
R: effective operation region
r1, r2: boundary line
r3: arc line
t: interval
Q: filling layer
U: ultrasound image

What is claimed is:
1. An ultrasound diagnostic apparatus, the ultrasound diagnostic apparatus comprising:
a transducer array;
a processor; and
a display device,
wherein the processor is configured to:
cause the transducer array to transmit an ultrasound beam toward a subject and receive an ultrasound echo generated inside the subject to acquire an ultrasound image, display on the display device the acquired ultrasound image,
analyze the acquired ultrasound image to detect a plurality of blood vessels and an insert in the ultrasound image,
specify a distance between each of the detected blood vessels and the insert,
determine whether or not each of the detected blood vessels is at a position reachable by the insert,
specify a closest blood vessel which has the specified distance smaller than a threshold value and is closest to the insert, among the blood vessels determined to be at the position reachable by the insert,
highlight only the closest blood vessel in a second form, and
highlight at least one of the remaining detected blood vessels in a first form different from the second form.

2. The ultrasound diagnostic apparatus according to claim 1,
wherein the second form is a form in which the closest blood vessel is highlighted while avoiding interference with the closest blood vessel.

3. The ultrasound diagnostic apparatus according to claim 2,
wherein the first form corresponds to at least one of a form in which the at least one of the remaining detected blood vessels is displayed to be filled with a highlight color, a form in which a contour of the remaining blood vessel is displayed in the highlight color, a form in which a character string is displayed at a position overlapping the remaining blood vessel, or a form in which an instruction mark of the at least one of the remaining detected blood vessels is displayed around the at least one of the remaining detected blood vessels, and the second form corresponds to at least one of a form in which the instruction mark is displayed around the closest blood vessel while being separated from the closest blood vessel in the ultrasound image, a form in which the closest blood vessel is enlarged and displayed, a form in which the closest blood vessel in the ultrasound image is displayed with brightness brighter than a vicinity, a form in which a filling layer of the highlight color set to have transmittance such that a tomographic image of the closest blood vessel is visible is displayed on the closest blood vessel in a superimposed manner, or a form in which the filling display of the closest blood vessel with the highlight color and the display of the tomographic image of the closest blood vessel are alternately repeated.

4. The ultrasound diagnostic apparatus according to claim 3, wherein the second form is the form in which the instruction mark is displayed around the closest form and the instruction mark of the second form is a frame line, which is a dotted line, surrounding the closest blood vessel.

5. The ultrasound diagnostic apparatus according to claim 3,
wherein, in a case where the specified distance is smaller than the threshold value and is smaller than a threshold value for enlarged display smaller than the threshold value, the processor enlarges and displays the closest blood vessel.

6. The ultrasound diagnostic apparatus according to claim 5,
wherein, in a case where the specified distance is smaller than the threshold value and is greater than the threshold value for enlarged display, the processor displays the instruction mark consisting of a frame line surrounding the closest blood vessel, around the closest blood vessel in a state in which an interval depending on the threshold value for enlarged display is provided between the closest blood vessel and the instruction mark.

7. The ultrasound diagnostic apparatus according to claim 5,
wherein the processor determines whether or not a part of the detected insert stays inside the closest blood vessel, and in a case where determination is made that a part of the insert stays inside the closest blood vessel, continues to enlarge and display the closest blood vessel while a part of the insert stays inside the closest blood vessel.

8. The ultrasound diagnostic apparatus according to claim 5,
wherein the processor determines whether or not a part of the detected insert stays inside the closest blood vessel, and in a case where determination is made that a part of the insert stays inside the closest blood vessel, stops the highlighting of the closest blood vessel.

9. The ultrasound diagnostic apparatus according to claim 1,
wherein the processor estimates an insertion direction of the detected insert, and
in determining whether or not each of the detected plurality of the blood vessels is at the position reachable by the insert, the processor performs the determination based on the estimated insertion direction.

10. The ultrasound diagnostic apparatus according to claim 2,
wherein, in a case where the insert is detected, the processor analyzes the ultrasound image to execute measurement processing regarding an insertion operation of the insert,
in the measurement processing, the processor measures items regarding the insertion operation of the insert which are different from the specified distance, and
the processor changes a display range or a display size in a case where the processor highlights the closest blood vessel in the second form, depending on a measurement result of the measurement processing.

11. The ultrasound diagnostic apparatus according to claim 10,
wherein the processor learns a correspondence relationship between the display range or the display size and the measurement result of the measurement processing, and
the processor highlights the closest blood vessel in the second form with the display range or the display size derived from the learned correspondence relationship and the measurement result of the measurement processing.

12. The ultrasound diagnostic apparatus according to claim 2, further comprising:
an input device to which identification information of an operator of the insert is input,
wherein the processor changes a display range or a display size in a case where the processor highlights the closest blood vessel in the second form, depending on information regarding the operator who is identified by the identification information input to the input device.

13. The ultrasound diagnostic apparatus according to claim 12, further comprising:
a recording device that stores, as the information regarding the operator, a use history of the ultrasound diagnostic apparatus by the operator to correspond to the identification information, wherein the processor reads out the use history corresponding to the identification information input to the input device from the recording device and changes the display range or the display size in a case where the processor highlights the closest blood vessel in the second form, depending on the read-out use history.

14. The ultrasound diagnostic apparatus according to claim 2, further comprising:
an input device to which setting information regarding a display range or a display size in a case where the processor highlights the closest blood vessel in the second form is input,
wherein the processor highlights the closest blood vessel in the second form with the display range or the display size that is indicated by the setting information input to the input device.

15. The ultrasound diagnostic apparatus according to claim 14,
wherein identification information of an operator of the insert is further input to the input device,
the ultrasound diagnostic apparatus further comprises a recording device that stores the setting information input from a certain operator in association with the identification information of the certain operator, and
in a case where the identification information is input to the input device, the processor reads out the setting information associated with the input identification information among the setting information stored in the recording device and highlights the closest blood vessel in the second form with the display range or the display size that is indicated by the read-out setting information.

16. The ultrasound diagnostic apparatus according to claim 1, further comprising:
an ultrasound probe having the transducer array,
wherein the ultrasound probe is connected to the processor,
the ultrasound diagnostic apparatus comprises a transmission circuit that causes the transducer array to transmit the ultrasound beam toward the subject and a reception circuit that processes a signal output from the transducer array having received the ultrasound echo generated inside the subject to generate a sound ray signal,
the processor generates the ultrasound image based on the sound ray signal generated by the reception circuit, and
each of the transmission circuit and the reception circuit is provided in the ultrasound probe or the processor.

17. A method of controlling an ultrasound diagnostic apparatus, the method comprising:
causing transmission of an ultrasound beam from a transducer array toward a subject and receiving an ultrasound echo generated inside the subject to acquire an ultrasound image;
displaying the acquired ultrasound image on a display device;
analyzing the acquired ultrasound image to detect a plurality of blood vessels and an insert in the ultrasound image;
specifying a distance between each of the detected blood vessels and the insert,
specifying a closest blood vessel which has the specified distance smaller than a threshold and is closest to the insert, among the detected blood vessels; and,
highlighting only the closest blood vessel in a second form and at least one of the remaining plurality of detected blood vessels in a first form different from the second form.

18. The method according to claim 17,
wherein the specifying the closest blood vessel comprises (i) determining whether or not each of the detected plurality of the blood vessels is at a position reachable by the insert, and (ii) selecting the closest blood vessel among the blood vessels determined to be at the position reachable by the insert through the process (i).

* * * * *